United States Patent
Caracci et al.

(10) Patent No.: US 7,286,221 B2
(45) Date of Patent: Oct. 23, 2007

(54) ARRAYED SENSOR MEASUREMENT SYSTEM AND METHOD

(75) Inventors: Stephen J. Caracci, Elmira, NY (US); Norman H. Fontaine, Painted Post, NY (US); Eric J. Mozdy, Elmira, NY (US); Po Ki Yuen, Corning, NY (US)

(73) Assignee: Corning Incorporated, Corning, NY (US)

(*) Notice: Subject to any disclaimer, the term of this patent is extended or adjusted under 35 U.S.C. 154(b) by 303 days.

(21) Appl. No.: 11/019,439

(22) Filed: Dec. 21, 2004

(65) Prior Publication Data

US 2005/0099622 A1 May 12, 2005

Related U.S. Application Data

(63) Continuation-in-part of application No. 10/602,304, filed on Jun. 24, 2003, now Pat. No. 7,057,720.

(51) Int. Cl.
*G01J 3/00* (2006.01)
(52) U.S. Cl. .......... 356/300; 356/364; 356/445
(58) Field of Classification Search ......... 356/300, 356/364, 445
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 5,071,248 A | 12/1991 | Tiefenthaler et al. | 356/128 |
| 5,313,264 A | 5/1994 | Ivarsson et al. | 356/73 |
| 5,479,260 A | 12/1995 | Fattinger | 356/361 |
| 5,738,825 A | 4/1998 | Rudigier et al. | 422/82.11 |
| 6,100,991 A | 8/2000 | Challener | 356/445 |
| 6,157,449 A * | 12/2000 | Hajduk | 356/364 |
| 6,346,376 B1 | 2/2002 | Sigrist et al. | 435/5 |
| 6,429,022 B1 | 8/2002 | Kunz et al. | 436/164 |
| 6,570,657 B1 * | 5/2003 | Hoppe et al. | 356/445 |
| 6,686,582 B1 | 2/2004 | Völcker et al. | 250/216 |
| 6,785,433 B2 | 8/2004 | Tiefenthaler | 385/12 |
| 7,151,598 B2 * | 12/2006 | Poponin | 356/301 |
| 2001/0021026 A1 | 9/2001 | Liu | 356/601 |
| 2001/0026943 A1 | 10/2001 | Dickopf et al. | 436/164 |
| 2001/0041843 A1* | 11/2001 | Modell et al. | 356/317 |
| 2001/0046050 A1* | 11/2001 | Hoyt | 356/417 |

(Continued)

FOREIGN PATENT DOCUMENTS

EP  0 202 021  11/1986

(Continued)

OTHER PUBLICATIONS

A. Bradenburg et al., "Grating couplers as chemical sensors: a new optical configuration", Sensors and Actuators B, vol. 17, 1993, pp. 35-40.

(Continued)

*Primary Examiner*—Gregory J. Toatley, Jr.
*Assistant Examiner*—Kara Geisel
(74) *Attorney, Agent, or Firm*—William J. Tucker; Thomas R. Beall

(57) ABSTRACT

Optical interrogation systems and methods are described herein that are capable of measuring the angles (or changes in the angles) at which light reflects, transmits, scatters, or is emitted from an array of sensors or specimens that are distributed over a large area 2-dimensional array.

16 Claims, 12 Drawing Sheets

U.S. PATENT DOCUMENTS

| | | |
|---|---|---|
| 2002/0001085 A1 | 1/2002 | Dickopf et al. ............. 356/445 |
| 2002/0109100 A1 | 8/2002 | Jackson, III et al. .... 250/458.1 |
| 2002/0127565 A1 | 9/2002 | Cunningham et al. ......... 435/6 |
| 2002/0168295 A1 | 11/2002 | Cunningham et al. ... 422/82.05 |
| 2003/0007896 A1 | 1/2003 | Tienfenthaler ............... 422/91 |
| 2003/0017580 A1 | 1/2003 | Cunningham et al. ... 435/287.2 |
| 2003/0017581 A1 | 1/2003 | Li et al. .................. 435/287.2 |
| 2003/0026891 A1 | 2/2003 | Qiu et al. ..................... 427/58 |
| 2003/0027327 A1 | 2/2003 | Cunningham et al. ... 435/287.2 |
| 2003/0027328 A1 | 2/2003 | Cunningham et al. ... 435/287.2 |
| 2003/0031596 A1* | 2/2003 | Tanaami ................. 422/82.08 |
| 2003/0032039 A1 | 2/2003 | Cunningham et al. ......... 435/6 |
| 2003/0059855 A1 | 3/2003 | Cunningham et al. ....... 438/7.9 |
| 2003/0068657 A1 | 4/2003 | Lin et al. .................... 435/7.9 |
| 2003/0077660 A1 | 4/2003 | Pien et al. ................... 435/7.1 |
| 2003/0092075 A1 | 5/2003 | Pepper ....................... 435/7.9 |
| 2003/0113766 A1 | 6/2003 | Pepper et al. .................. 435/6 |
| 2003/0133640 A1 | 7/2003 | Tiefenthaler ................ 385/12 |
| 2004/0132172 A1 | 7/2004 | Cunningham et al. ... 435/287.2 |
| 2004/0132214 A1 | 7/2004 | Lin et al. .................... 436/518 |
| 2004/0151626 A1 | 8/2004 | Cunningham et al. ........ 422/58 |
| 2004/0223881 A1 | 11/2004 | Cunningham et al. ... 422/82.05 |

FOREIGN PATENT DOCUMENTS

| | | |
|---|---|---|
| EP | 1 271 219 | 1/2003 |
| WO | WO 90/09560 | 8/1990 |

OTHER PUBLICATIONS

R. Horváth et al., "Demonstration of reverse symmetry waveguide sensing in aqueous solutions", Applied Physics Letters, vol. 81, No. 12, Sep. 16, 2002, pp. 2166-2168.

W.A. Challener et al., "A multilayer grating-based evanescent wave sensing technique", Sensors and Actuators B, vol. 71, 2000, pp. 42-46.

F.F. Bier et al., "Real-time measurement of nucleic-acid hybridization using evanescent-wave sensors: steps toward the genosensor", Sensors and Actuators B., vols. 38-39, 1997, pp. 78-82.

U.S. Appl. No. 10/602,304, Caracci et al., filed Jun. 27, 2003.
U.S. Appl. No. 10/993,565, Fontaine et al., filed Nov. 18, 2004.
U.S. Appl. No. 11/027,509, Caracci et al., filed Dec. 29, 2004.
U.S. Appl. No. 11/100,199, Fontaine et al., filed Apr. 5, 2005.

* cited by examiner

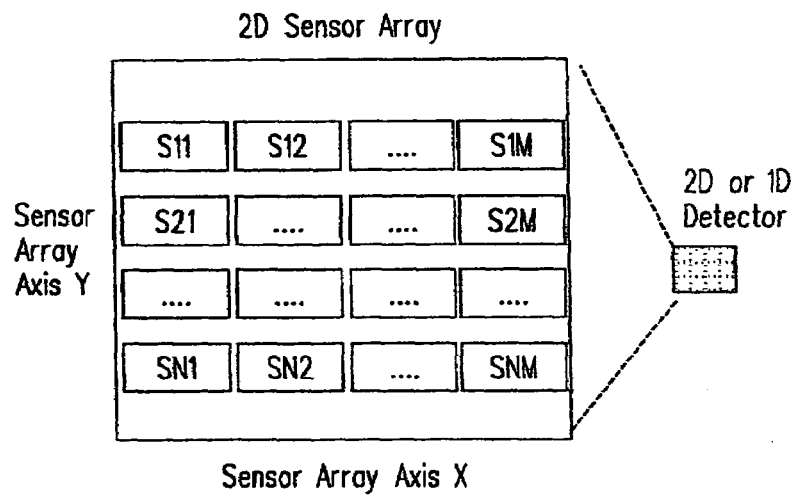
FIG. 1A
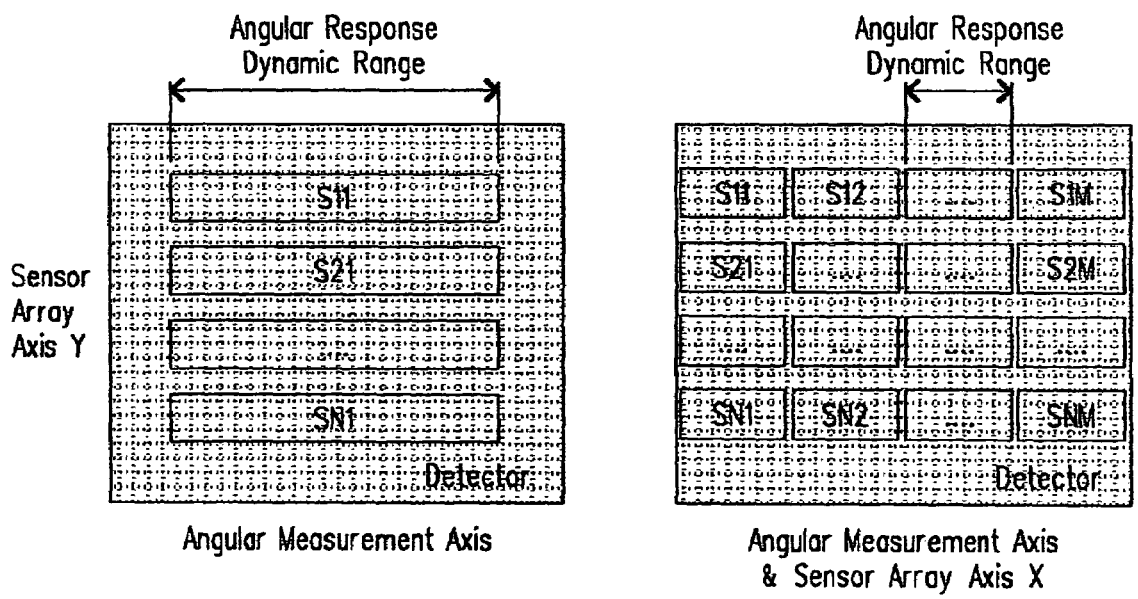
FIG. 1B
FIG. 1C

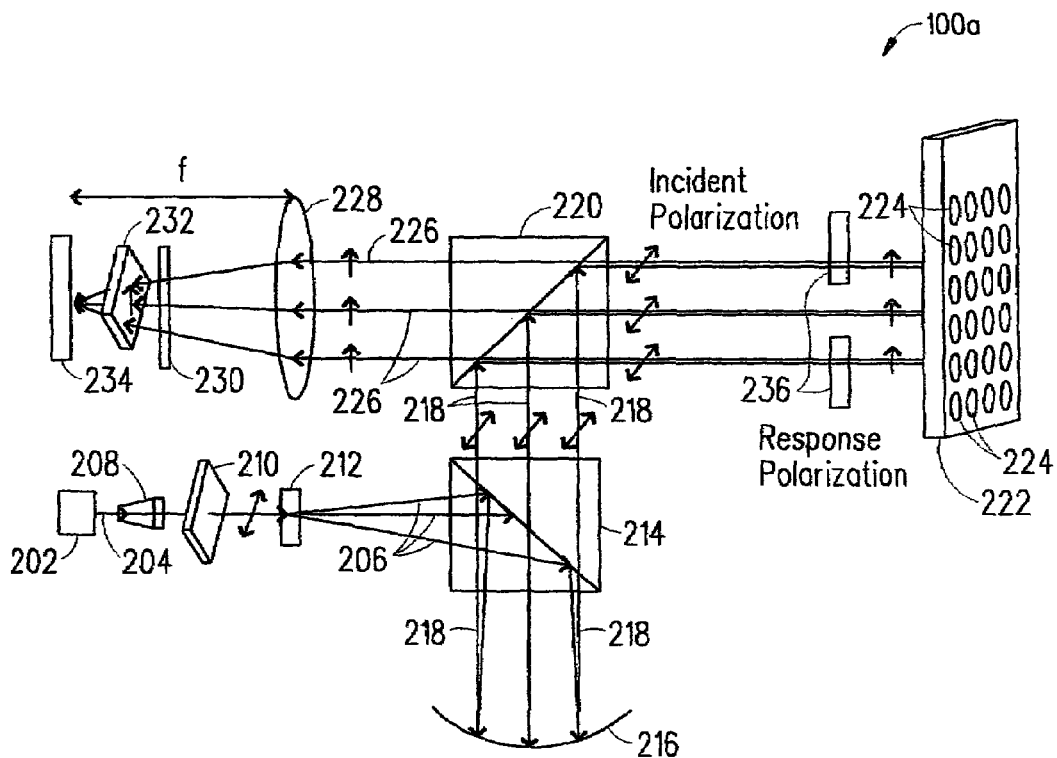
FIG. 2
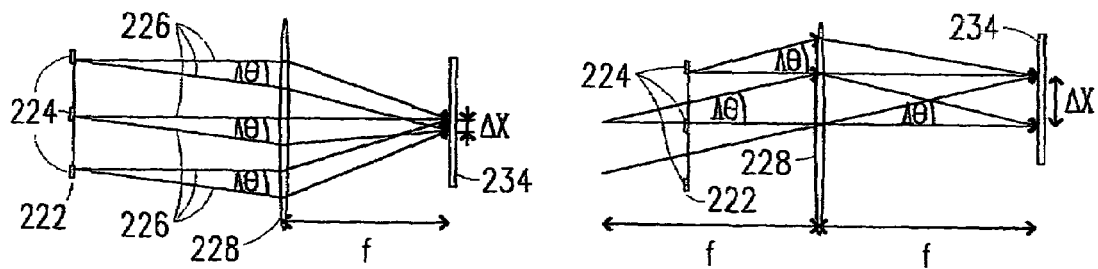
FIG. 3A
FIG. 3B

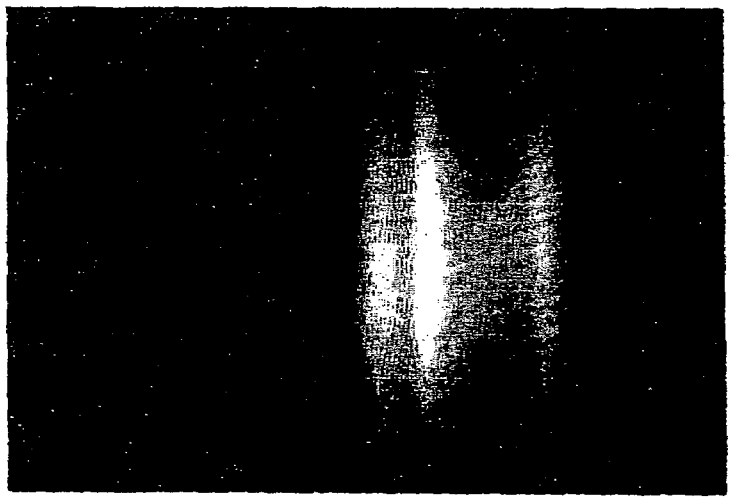
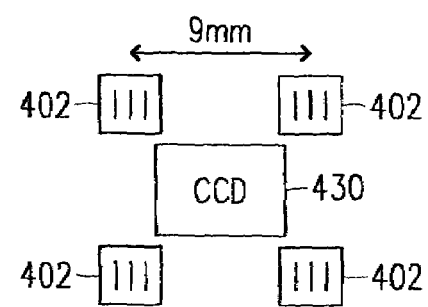
FIG. 5A                    FIG. 5B
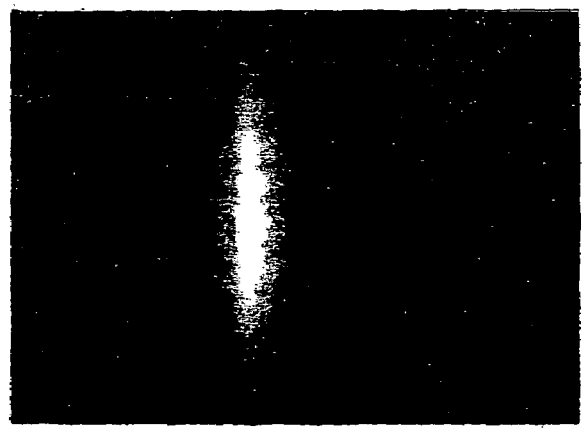
FIG. 6A

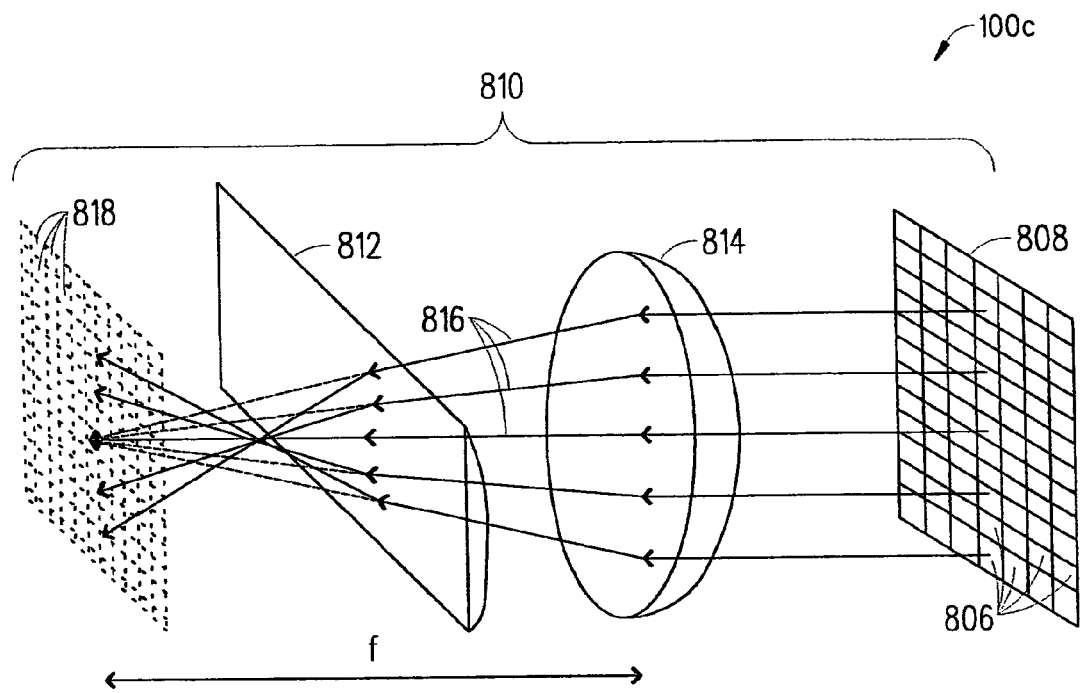
FIG. 8B
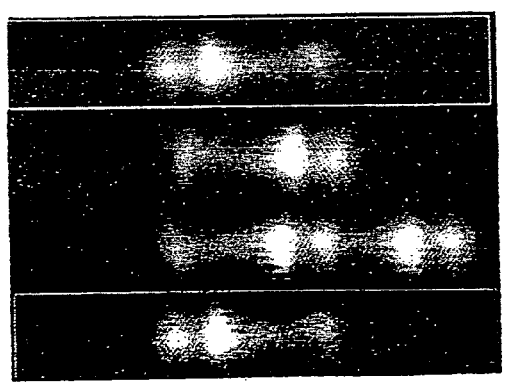
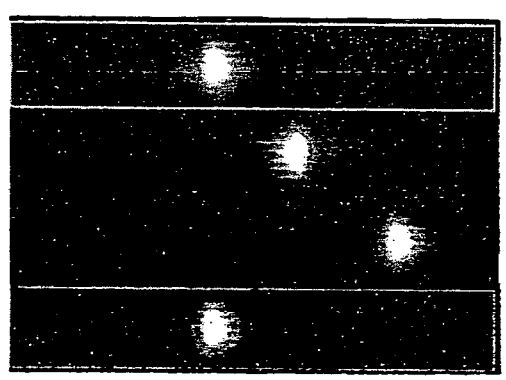
FIG. 9A  FIG. 9B

ARRAYED SENSOR MEASUREMENT SYSTEM AND METHOD

CROSS REFERENCE TO RELATED APPLICATION

This application is a continuation-in-part application of U.S. patent application Ser. No. 10/602,304, filed Jun. 24, 2003 now U.S. Pat. No. 7,057,720 the contents of which are incorporated herein.

BACKGROUND OF THE INVENTION

1. Field of the Invention

The present invention relates to different types of optical interrogation systems and methods capable of interrogating a two-dimensional (2D) array of optical sensors (e.g., grating coupled waveguide sensors) located for example in a multiwell plate.

2. Description of Related Art

Today there is considerable interest in developing instrumentation to enable high throughput screening (HTS) of bio-chemical interactions or binding events using optical sensors located in standardized multiwell plates. The targeted applications include drug discovery and screening, laboratory diagnosis, and fundamental research. The advantage of the standard multiwell plate format is that it allows existing automated HTS and manual fluid handling systems to be used in conjunction with novel biosensing elements. The most desirable standardized formats are 96 multiwell plates (9 mm specimen spacing), 384 multiwell plates (4.5 mm specimen spacing), and 1536 multiwell plates (2.25 mm specimen spacing). All of these multiwell plates cover the same rectangular area of roughly 100 mm×70 mm.

Two different types of optical interrogation systems can be used to detect bio-chemical interactions on optical sensors (e.g., surface grating sensors) which are located in multiwell plates. One type of interrogation system is a spectral interrogation system which requires the use of a collimated excitation source that spans or scans through a broad spectral width. The spectral interrogation system also has a receive system which detects changes in the wavelengths associated with the sensor's response to surface chemistry binding. The other type of interrogation system is an angular interrogation system which requires the use of an excitation source (such as a laser) that has a narrow spectral width and spans or scans through a broad range of angles. The angular interrogation system also has a receiver system which detects changes in the angles associated with the sensor's response to surface chemistry binding.

In order to achieve the highest sensitivities and, simultaneously the greatest measurement speed, it is best to measure the fewest number of points possible on the response curve from each sensor and then to fit that curve to determine the response location with sub-sampling (or sub-pixel) accuracy. Typically the minimum number of points required for sampling the response curve with best efficiency is to have on the order of 6 to 10 points lying above the full-width-at-half-maximum (FWHM) of the measured response peak. Fitting of the response may be carried out after filtering the measured response curve, although filtering may not be necessary. Using these fitting methods it is frequently possible to achieve measurement sensitivities on the order of $1/100^{th}$ of a sampling interval (or pixel). When the requirement for sensitivity approaches this level of sub-sampling resolution, repeatability of the locations sampled on the response curve, as well as the locations interrogated on each sensor, must be ensured to a very high degree. Hence any system which does not require movement or scanning of critical components (e.g. the optical beam, the sensor array, or the receive optics) will have a distinct advantage in sensitivity, repeatability, and speed over systems which do require scanning of critical components.

Scanning methods may be avoided by using highly multiplexed methods, where numerous sets of optical components are dedicated to measuring each of a few individual sensors out of the complete array. However, highly multiplexed systems require many duplicate components, such as lasers, optics, fiber optics, and detectors which can be expensive and complex to construct. In general, it is practical to implement multiplexed optical solutions when the number of sensors to be measured is on the order of tens. However, as the number of sensors in the array approaches 100 or more, these highly multiplexed methods frequently suffer from difficult and high cost of development and construction, poor reliability due to the numerous components, poor uniformity of measured response performance across the array sensors, and difficult serviceability of individual components. Hence measurement systems that use the fewest number of parts and yet enable measurement of every sensor in the array will have a distinct advantage over highly multiplexed systems with regards to manufacturability, reliability, and serviceability.

In another aspect of HTS, single and multi-step assays are often conducted on many different multiwell plates. As an example, for surface index optical sensors, it may be necessary to bind a reactant to a surface, incubate for a period of time, wash the unbound reactant from the sensor, make a reference measurement, introduce a binding-specific specimen of interest, incubate again, wash again, and then measure again to identify a specific binding result. The time scales for each step can be anywhere from seconds to hours. Hence, measurement systems may be required to shuffle many different multiwell plates in and out of the measurement area by either manual or automated plate handling systems. In these situations shifts in the measurement response due to plate replacement need to be measured so that they may be compensated in the measurement results.

Today, systems which use an angular or spectral interrogation approach are developed by utilizing any of the following methods:

(a) Highly Multiplexed Method:

The advantage of this approach is that the critical components can be fixed, thus eliminating the accuracy limitations frequently encountered in a scanning apparatus due to re-positioning errors. However, as described above, when the number of sensors in the array approaches 100 or more, the multiplexed approach frequently suffers from difficult and high cost of construction, poor reliability due to the numerous components, poor uniformity of measured response performance across the array sensors, and difficult serviceability of individual components.

(b) Motion Based Scanning Method:

This method decreases the number of components, cost, and complexity of the instrument by moving critical elements to new positions each time a single or a group of sensors is measured. However, the repeatability of the re-positioning is often the limiting factor in the ability to measure responses with sub-sampling accuracy. In addition, the need to move rapidly to a new specimen location that is a large distance from the previous position (e.g. millimeters) and doing so repeatedly and with high repositioning accuracy (e.g. 100 nm) results in conflicting design requirements for the positioning equipment. These competing requirements necessitate high quality and high cost positioning hardware. Frequently array scanning speed must be sacrificed greatly to ensure an array scanning system's accuracy and repeatability.

(c) Source/Receiver (Angle or Wavelength) Scanning Methods:

These methods either scan the input angle/wavelength or the detected angle/wavelength and measures the response versus time. Such a time division method enables the use of simple and small area optical detectors or allows the mapping of numerous sensors in the array to a smaller area detector. However, when a large dynamic range must be scanned accurately, the time window occupied by the response signal is decreased relative to the entire scan duration, given a fixed (constrained) total scan time. The resulting loss of signal integration time creates an inefficiency that must be compensated for by higher optical power from the source and/or decreased scanning rates. Frequently the repeatability of the scanning limits the sensititivity of the scanning apparatus.

(d) Large Area Components:

This method uses very large area light sources (flood illumination or source arrays) or very large receive components (for example large area CCDs) to simultaneously measure all or a large group of sensors. Unfortunately, large area detector components are very expensive and suffer from slower read out rates when compared to small area detectors. In addition, the use of very large area light sources to illuminate the array can result in power distribution that is severely under-utilized by the sensors in the array. This is particularly true for arrays that contain small area sensors with larger inter-sensor spacing. When using flood illumination, signals associated with multiple sensors or the areas surrounding the sensors often overlap at the detector(s) which causes cross-talk between sensor signals, or interference distortion in the measured response. This interference can limit the accuracy of the measured response of the sensors, particularly when sub-sampling resolution is required.

(e) Array Image Reduction and Mapping Method:

This method maps the responses from locations in the 2-dimensional array of sensors onto a smaller 2-dimensional optical detector. This has the advantage of allowing fewer and smaller area detectors by mapping the different regions of the array to the detector. However, for 2-dimensional array formats, the dynamic range available at the detector for measurement of each sensor's response must be reduced to avoid cross-talk in the detected signals. Also, in this image reduction method, "ghost reflections" may be condensed onto the detector and partially overlap with the desired primary signal. These interference effects then decrease the ability to measure with sub-sampling accuracy.

(f) Array Size Reduction Method:

This method has the advantage of decreasing the total array size that must be measured and with it the dimensions of the corresponding optical hardware and detectors. However, the increase in density of the arrays makes it much more difficult to process and handle the sensors. Array size reduction can require miniaturized components and precision handling. Moreover, this reduction in size does not solve the dynamic range issues associated with approach (e) and can result in increased signal cross-talk of sensor signals at the detector. Furthermore, array size reduction may be contrary to the compatibility requirements associated with standard large area array formats.

It should be noted that combinations of the elements in these six main interrogation approaches (a)-(f) are possible. However, the resulting interrogation system would then have the combined associated advantages, complications and drawbacks described above.

Referring to FIGS. 1A-1C, there are three block diagrams that help illustrate some of the drawbacks associated with the traditional approaches (a)-(f) for interrogating a large two-dimensional array of optical sensors. FIG. 1A shows the problem at hand: large area 2D arrays of optical sensors (S) are measured by using a small area 2D or 1D detector. One approach (b) that is used to try and overcome this problem is shown in FIG. 1B where a row or column of sensors (e.g. S11 . . . SN1 on axis Y) are mapped to the response area of the detector and then critical components are repositioned (scanned) to measure the next column (e.g. S12 . . . SN2) or row of sensors with the same detector area. However, the repeatability of the re-positioning of those critical components is often the limiting factor in the ability of this approach to measure responses with sub-sampled (sub-pixel) accuracy. Another approach (e) that is used to try and overcome this problem is shown in FIG. 1C where the image of the array responses is reduced optically onto the detector. However, presuming a fixed sampling resolution of the detector, this decreases the resolution available to measure each sensor's response relative to the solution of FIG. 1B. This approach of reducing the image also increases the effects of interference from over-lapping of ghost reflections in the system, and possibly sensor cross-talk. Yet another approach (not shown) used to solve this problem is to reduce the image of the array onto the detector and then scan the input or receive angles. Again, it is not desirable to scan critical components, the optical input beam angle, or the receiver angle. Below are listed several patents and publications that describe in greater detail different types of traditional angular interrogation systems:

1) US2003/0007896A1, "Optical Sensor and Optical Process for the Characterization of a Chemical and/or Bio-chemical Substance," K. Tiefenthaler, Jan. 9, 2003.
2) US2003/0133640 A1, "Waveguide Grid Array and Optical Measurement Arrangement," K. Tiefenthaler, Jul. 17, 2003.
3) U.S. Pat. No. 5,071,248, "Optical Sensor for Selective Detection of Substances and/or for the Detection of Index of Refraction Changes in Gaseous, Liquid, Solid, and Porous Samples," K. Tiefenthaler et al., Mar. 28, 1989.
4) U.S. Pat. No. 5,479,260, "Optical Process and Apparatus for Analysis of Substances on Sensor Surfaces," C. Fattinger, Dec. 26, 1995.
5) U.S. Pat. No. 6,100,991, "Near Normal Incidence Optical Assaying Method and System having Wavelength and Angle Sensitivity," Challener et al., Aug. 8, 2000.
6) "Grating couplers as chemical sensors: a new optical configuration," A. Brandenburg and A. Gombert, Sensors and Actuators B, 17 (1993) 35-40.
7) "Real-time Measurement of Nucleic-acids Hybridization Using Evanescent-wave Sensors: Steps Towards the Genosensor," F. Bier et al., Sensors and Actuators B 38-39, (1997) 78-82.
8) "A multilayer grating-based evanescent wave sensing technique," W. A. Challener, et al., Sensors and Actuators B 71 (2000) 42-46

9) "Demonstration of Reverse Symmetry Waveguide Sensing in Aqueous Solutions," R. Horvath et al., App. Phys. Lett., Vol 81, No 12, 16 September 2002, pp 2166-2168

10) U.S. Pat. No. 6,346,376, "Optical Sensor Unit and Procedure for the Ultra-sensitive Detection of Chemical or Biochemical Analytes," H. Sigrist et al., Feb. 12, 2002.

11) U.S. Pat. No. 6,429,022 B1, "Integrated-optical Sensor and Method for Integrated-optically Sensing a Substance," R. Kunz et al., Aug. 6, 2002.

12) U.S. Pat. No. 5,313,264, "Optical Biosensor System," B. Ivarsson et. al., May 17, 1994.

13) US20010026943A1, "SPR Sensor System," S. Dickopf et al., Oct. 4, 2001.

14) US2002/00001085 A1, "Set-up of Measuring Instruments for the Parallel Readout of SPR Sensors," S. Dickopf et al., Jan. 3, 2002.

The contents of these patents, patent applications and publications are incorporated by reference herein.

It should be appreciated that several of these patents, patent applications and publications do describe angular interrogation systems that can measure the angular responses from arrays of optical sensors. For instance, traditional angular interrogation systems that re-position the sensors (see ref. 10) or that move or switch critical optical components such as laser sources (see ref. 11) have been detailed. However, the action of switching or moving critical components creates measurement errors that can dominate the level of sensitivity and/or speed that is achievable by the measurement system. Moreover, a traditional angular interrogation system that uses an anamorphic optical receive system for Surface Plasmon Resonance (SPR) measurements is described in ref. 12. However, that system can either a) measure 1-dimensional arrays of sensors, where scanning must be used to address the other dimension of sensors in an array format, or b) image the 2D array of responses from the 2-D sensor array onto the detector area, which limits the resolution available for measuring each sensor's response. Other SPR array angular interrogation systems use array size reduction or image reduction methods for directing responses from two dimensional arrays onto small area detectors (see ref. nos. 13 and 14). However, these types of reduction methods must resort to scanning of the angle (or wavelength) to trace the sensor response functions for the array and as such they have the problematical dynamic range and repeatable scanning issues. As can be seen, it is not easy to scale the systems of these different interrogation approaches (a)-(f) to enable practical high speed and high sensitivity measurements of large arrays of sensors. This need and other needs are satisfied by the optical interrogation systems and methods of the present invention.

BRIEF DESCRIPTION OF THE INVENTION

The present invention includes several embodiments of optical interrogation systems and methods capable of measuring the angles (or changes in the angles) at which light reflects, transmits, scatters, or is emitted from an array of sensors or specimens that are distributed over a large area 2-dimensional array. In one embodiment of the present invention, the optical receive system has a configuration that will be familiar to those skilled in optics as the same type used for far-field diffraction measurements. This optical arrangement uses a lens in reversed auto-collimation mode such that the detector can simultaneously receive the light from sensors in all or a sub-section of a sensor array at a detector. This receive configuration has the advantage that all responses emanating from the same angle anywhere on the surface of the sensor array will be mapped to the same location on the detector, thus allowing the smallest area detector to be used to measure the angular response of all sensors. By itself, this configuration would be problematic because all of the signals from every sensor in the array would map to the same location on the detector. However, a simple mask may be used to select which sensor is illuminated and this mask may be scanned rapidly and with low precision to allow serial interrogation of every sensor in the array. In another embodiment of the present invention, the optical interrogation system incorporates an anamorphic optical receive system that enables simultaneous detection of angular responses from rows or columns of sensors in the 2D array. In yet another embodiment of the present invention, the optical interrogation system incorporates an angular measurement system which measures the change in angular tilt of the sensor plane when the sensor array is moved or removed and then replaced in the measurement system. In this embodiment, the optical interrogation system can combine both the mechanical tilt and the sensor response angle measurement functions into a single instrument to compensate for systematic errors in the angular response measurement that might be caused by the re-positioning or removal and re-insertion of the sensor array. Several other embodiments of optical interrogation systems are also described herein.

BRIEF DESCRIPTION OF THE DRAWINGS

A more complete understanding of the present invention may be had by reference to the following detailed description when taken in conjunction with the accompanying drawings wherein:

FIGS. 1A-1C are three block diagrams which are used help describe some of the drawbacks associated with using traditional angular optical interrogation systems to interrogate two-dimensional arrays of optical sensors;

FIG. 2 is a block diagram of one embodiment of an optical interrogation system that has a far-field diffraction measurement configuration in accordance with the present invention;

FIGS. 3A-3B are two block diagrams that show some of the components in a receive side of the optical interrogation system shown in FIG. 2 where a focusing optic is used in reversed auto-collimation mode in a manner that is typical of a far-field diffraction measurement wherein this mode enables a single small area detector to simultaneously receive and measure only the angular response from all or a sub-section of sensors in a sensor array;

FIGS. 5A and 5B illustrate an image of angular reflection resonance data from three sensors and a block diagram of the relative size and placement of the sensors in relation to the size of the CCD detector wherein this data was obtained in an experiment when the mask was not used in the optical interrogation system shown in FIG. 4;

FIGS. 6A-6C illustrates an image and two graphs of angular reflection resonance data that were obtained in another experiment when the mask was used to block the illumination of two out of the three sensors from FIG. 5 in the optical interrogation system shown in FIG. 4;

FIGS. 8A and 8B are block diagrams of a launch system and an anamorphic receive system that are used in an optical interrogation system that is configured in accordance with a third embodiment of the present invention;

FIGS. 9A and 9B are two simulation images used to help describe the operation of the anamorphic receive system shown in FIG. 8B;

DETAILED DESCRIPTION OF THE DRAWINGS

Figure 4:
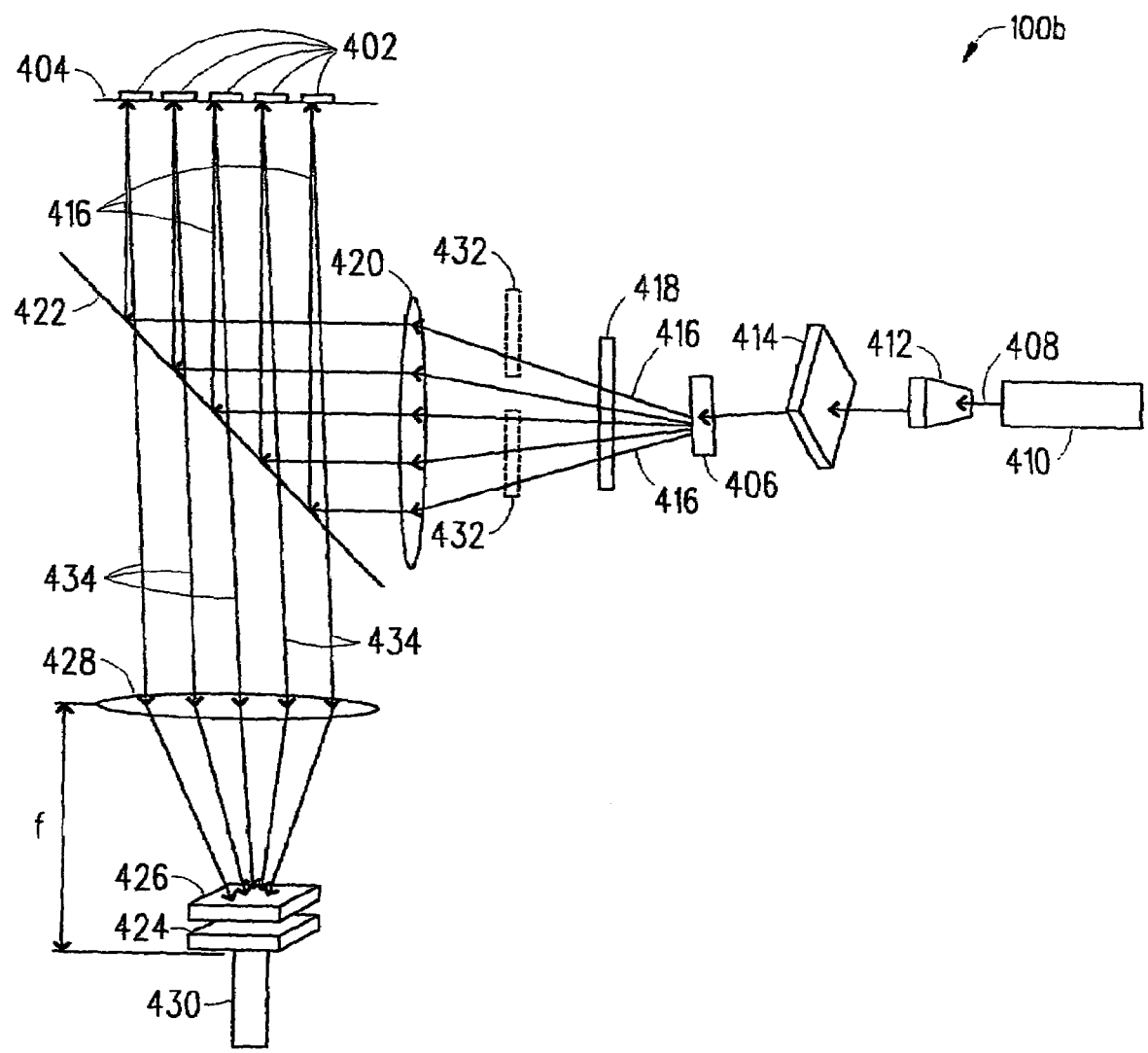
FIG. 4 is a block diagram of a second embodiment of an optical interrogation system that uses a lens and a single beamsplitter on the launch end and that has the same type of far-field diffraction receive configuration in accordance with the present invention.

Referring to FIGS. 2-13, there are disclosed in accordance with the present invention several embodiments of an optical interrogation system 100 that can be used to interrogate an array of sensors or specimens that are distributed over a large area 2-dimensional array. It should be readily appreciated by those skilled in the art that the optical interrogation system 100 can be used to interrogate a specimen array to determine whether or not a biological substance such as a cell, molecule, protein, drug, chemical compound, nucleic acid, peptide or carbohydrate is present within anyone of the specimens in the specimen array. The optical interrogation system 100 can also be used to perform other label or label-free studies such as photoluminescence assays, fluorescence assays, scattering assays, absorbance assays, cell migration assays, drug permeability assays, drug solubility studies, virus detection studies and protein secretion studies. Accordingly, the optical interrogation system 100 and methods for using the optical interrogation system 100 should not be construed in a limited manner.

Referring to FIG. 2, there is shown a block diagram of one embodiment of an optical interrogation system 100a that has a far-field diffraction measurement configuration in accordance with the present invention. This embodiment is one that might be used for measurement of surface-grating sensors. As shown, the light source 202 emits a light beam 204 that is divided into a 2-dimensional array of beamlets 206 by a diffractive optic element 212. A beamlet conditioning optic 208 is shown placed prior to the diffractive optic 212 to simultaneously tailor all of the numerical apertures and spot sizes of the array of beamlets 206 at the sensor array 222. A polarizer 210 is shown placed between the beamlet conditioning optic 208 and the diffractive optic 212 which ensures control the polarization state of all the beamlets 206. Then a non-polarizing beamsplitter 214 is used to direct the diverging beamlets 206 to a spherical mirror 216. The spherical mirror 216 is placed such that the focal length of the spherical mirror 216 is located at the diffractive optic 212 which enables it to collimate the beamlet propagation axes. The focal length of the spherical mirror 216 is chosen such that the reflected beamlets 218 have the desired inter-beam separation. If needed, a lens (not shown) may be placed in the path of the diverging beamlets 206, prior to the beamsplitter 214, to allow fine adjustment of the effective focal length of the spherical mirror 216. The collimated beams 218 pass back through the non-polarizing beamsplitter 214 to another non-polarizing beamsplitter 220. The second non-polarizing beamsplitter 220 directs the beamlets 218 to the sensor array 222. The sensors 224 in the sensor array 222 are oriented at 45° to the incident polarization such that the reflected signal response polarization from the grating sensor is rotated by 45° relative to the incident polarization. Alternatively, the second non-polarizing beamsplitter 220 may be a polarizing beam splitter. The response and other surface reflections 226 from the optical sensors 224 return through the second beam splitter 220 where one-half of this light is passed. A focusing optic 228 receives this light 226 and directs it through a bandpass filter 230 (to reject ambient light) and through an analyzer 232 to a detector 234. The detector 234 is in the far-field diffraction measurement configuration when it is placed at the focal length "f" of the focusing optic 228. In this configuration, the focusing optic 228 directs the angular response light 226 from all locations on the sensors 224 in the specimen array 222 to the same pixel locations on the detector 234. A mask 236, which can be moved or switched, functions to block the optical responses from all sensors 224 except those sensors 224 that are to be measured. The mask 236 can be placed anywhere in the system 10a where the beamlets are sufficiently separated that they may be selectively blocked by the mask. The analyzer 232 eliminates surface reflections from the optical surfaces 204, 214, 220, 222, 228 and 230 (for example) that lie between the light source 202 and the detector 234. The components 214 and 220 (for example) should be anti-reflection coated wherever, possible to diminish any undesirable surface (ghost) reflections. This optical interrogation system 100a was used to obtain the data in FIGS. 10 and 13D-F (described below).

FIGS. 3A-3B show the conceptual basis of the receive side of the optical interrogation system 10a without the second non-polarizing beamsplitter 220, the bandpass filter 230 and the analyzer 232. The focusing optic 228 is used so that the detector 234 can simultaneously receive the light 226 from sensors 224 in all or a sub-section of the sensor array 222. As can be seen in FIGS. 3A-3B, the detector 234 is placed at or near to the focal length "f" of the focusing optic 228 which is in a reversed auto-collimation mode. This configuration maps the far-field angular position θ of a reflection or beamlet 226 from a sensor 224 anywhere within the array 222 to the same location X on the detector 234. In particular, if the angle of reflection θ from any sensor 224 changes by an amount Δθ then the light 226 from that sensor 224 will be directed to a different location X+ΔX on the detector. As shown in FIG. 3B, this configuration has the added advantage that the plane of the sensor array 222 can be located anywhere (or at least with low tolerance) along the optical axis of the receive system without altering this mapping relationship. FIG. 3B also shows that Δx=f tan (Δθ)~fΔθ for all sensors in the array.

Referring to FIG. 4, there is shown a block diagram of a second embodiment of an optical interrogation system 100b that has a far-field diffraction measurement configuration in accordance with the present invention. In this diagram of one working embodiment, the sensors 402 were spaced on a 96 sensor array 404 with 9 mm spacing in both directions between the sensors 402. A 7×7 diffractive optic 406 was used to split the light 408 from a 3 mW laser diode 410 which passed through a beamlet conditioning optic 412 and a polarizer 414 into a square array of 49 beamlets 416, each of which comprise approximately 60 µW of power. The power in each beamlet 416 was further attenuated by 0.8 dB with a neutral density (ND) filter 418. The auto-collimating optic 420 was a simple plano-convex lens pair with an effective focal length of 270 mm. (Ideally this lens 420 should be an F-θ telecentric lens or optic.) The beam splitter 422 was used to direct all of the beamlets 416 simultaneously at the plane of the sensor array 404 with one beamlet 416 at each sensor 402. The polarizer 414 was used to make the polarization at all of the sensors 402 in the sensor array 404 equal to 45° relative to the grating lines in the sensors 402. The analyzer 424 was oriented at 90° relative the polarizer 414 and 450 relative to the grating lines in the sensors 402. This helped to eliminate reflections from other optical surfaces that are not associated with the grating waveguide reflection resonances from the sensors 402. The 20 nm bandpass filter 426 passes the wavelength of light 408 associated with the laser 410 and rejected stray light. The focal length "f" of the reverse auto-collimating focusing optic 428 was 175 mm, and the plane of the CCD detector 430 was placed at the focal point of this lens 428. The CCD detector 430 spanned 6.4 mm×4.8 mm. It should be noted that optical interrogation system 100b is similar to optical interrogation system 100a except that a lens 420 is used instead of a mirror 216 and beamsplitter 214 as shown in FIG. 2. However, the mirror 216 is preferable because it is free from all chromatic aberrations, thus allowing any wavelength of light to be used in the optical interrogation system 100a. The optical interrogation system 100b was used to obtain the data in FIGS. 5-8 (described below).

FIGS. 5A and 5B illustrate a block diagram and image of angular reflection resonance data that was obtained in an experiment when the mask 432 was not used in the optical interrogation system 100b. In particular, FIG. 5A is a photo illustrating the angular resonance reflections from three grating-coupled sensors 402 that were imaged simultaneously onto the CCD detector 430 (resonance from the fourth sensor 402 was not observed). And, FIG. 5B is a block diagram illustrating the spacing between the sensors 402 that was 9 mm in both directions, which is greater than the dimensions of the CCD detector 430. Although not shown it should be noted that if there was an angular shift in the resonance angle from an individual sensor 402 in response to a surface index of refraction change at that sensor 402 then one of the bright intensity lines would be displaced horizontally in the image shown in FIG. 5A.

Figure 6B:
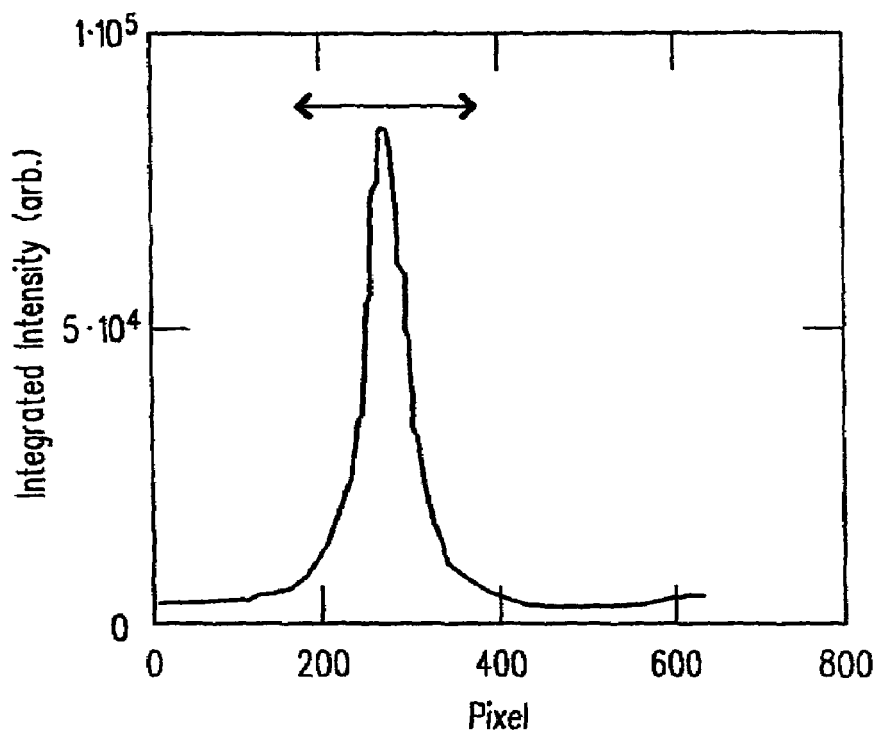
Figure 6C:
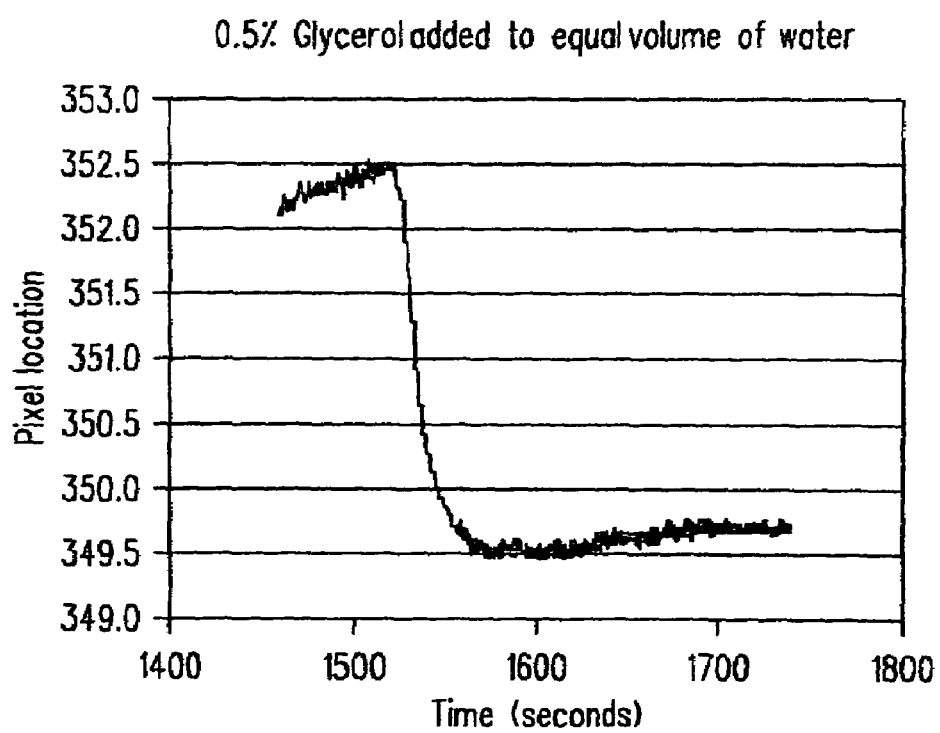

FIGS. 6A-6C illustrates A) an image of the resonant response from one grating sensor, B) the result of integrating that image along the vertical direction, and C) the location of the resonant response when exposed to a change in the bulk index of refraction at the surface of the sensor. The mask 432 was used in the optical interrogation system 100b to make the image in FIG. 6A. The mask 432 allowed a single beam 434 from the beamlet array 416 to illuminate a single sensor in the array. This mask 432 may be switched through a series of positions or states to enable the reflected light 434 from each sensor 402 to illuminate each sensor serially in time and allow measurement by the same stationary detector 430. FIG. 6A is a photo illustrating the angular resonance reflections from one grating-coupler sensor 402 that was imaged onto the CCD detector 430. In this experiment, the images from the CCD detector 430 were summed 10 times per temporal data point at a rate of 30 frames per second. This image data was then summed along the vertical direction of the CCD detector 430 to produce the resonance curve shown in FIG. 6B. A fitting algorithm was then used on the peak to track the resonance shift with sub-pixel resolution. An equal volume of Glycerol-water solution with weight concentration of 0.5% was added to a pure water sample on the corresponding sensor 402, resulting in a dilution to 0.25% and a corresponding index of refraction change at the sensor surface of $3*10^{-4}$. This resulted in a shift of the resonance of approximately Δx=3 pixels at the CCD detector 430 shown in the graph of FIG. 6C. As can be seen, the noise (1 std. deviation of the baseline noise after linear background subtraction) was 0.02 pixels and the pixel spacing was 8.4 µm per pixel along the pixel axis. This noise result equates to a response displacement sensitivity at the CCD detector 430 of 170 nm, an angular shift sensitivity of 0.96µ radians, and a $2*10^{-6}$ index of refraction sensitivity (see equation nos. 1 and 2).

Figure 7:
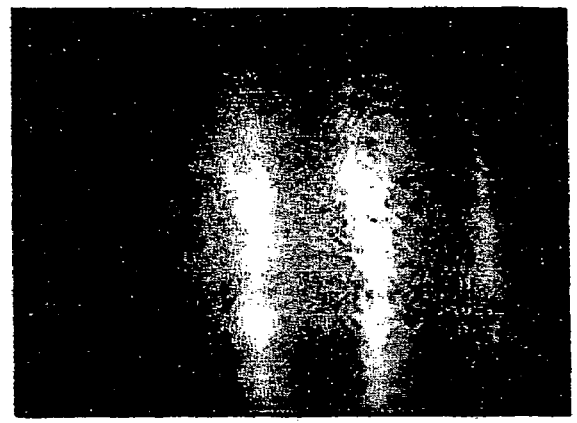
FIG. 7 is an image of six resonances from a 3×3 grid of neighboring sensors with 9 mm inter-sensor spacing that were interrogated simultaneously in yet another experiment where the mask was not used in the optical interrogation system shown in FIG. 4.

FIG. 7 is an image of six resonances from a 3×3 grid of neighboring sensors 402 that were imaged and detected simultaneously in yet another experiment where the mask 432 was not used in the optical interrogation system 100b. Three resonances overlay each other in the bright stripe at the left, two resonances can just be discerned at the top of the image overlaying each other in the middle stripe, and one resonance lies on the right. These six resonances originated from six sensors 402 spanned a length of 18 mm in both directions at the sensor array 404. The interference (crosstalk) between the 6 over-lapping resonances caused significant distortion in this image, but it could be eliminated for each sensor 402 by using the mask 432.

It should be noted that when the resonant response from a sampled location changes its angle (for example, due to an index of refraction change at the surface of a sensor 402) then the effect will be to displace the resonant reflection angle across the plane of the CCD detector 430 (see FIGS. 5-7). Thus an angular change in the light 434 originating or reflecting from any sensor 402 location within the sampled section of the array 404 is detectable as a displacement of signal intensity at the plane of the CCD detector 430.

Using the small angle approximation tan(Δθ)~Δθ, an angular reflection change Δθ corresponds to a measured position shift of Δx at the CCD detector 430 that is equal to:

$$\Delta\theta = \Delta x / f \quad (1)$$

Hence, all of the sensors 402 in an array 404 can be read by use of a single and relatively small area detector 430. Equation No. 1 shows that additional resolution (smaller Δθ) can be obtained by increasing the focal length f of the lens 428 if the angular measurement resolution is limited by the angular response change of the resonance or the pixel size of the detector 430. Equation No. 1 also shows that additional angular dynamic range may be obtained on a detector 430 of fixed size by decreasing the focal length of the receive lens 428.

This technique of far-field imaging of the diffraction pattern from all of the sensors 402 to the plane of the sensor array 404 should be contrasted with that of imaging the actual sensors 402 at the plane of the detector 430. In the case of the sensor imaging technique, the response of each sensor location would occupy a different location at the detection plane as shown in FIG. 1C. In the present description, the angular response of all of the sensors 402 or some fraction of sensors 404 occupy the same location on the detector plane 430 (see FIGS. 5A and 7). Thus, to read the signal from any one location within the sensor array 404, the beamlets from all of the other locations may be blocked with a simple mask 432 (see also FIG. 2). This mask 432 can be scanned so as to pass only a single beamlet or a group of beamlets using a simple, low precision, high speed scanning apparatus, such as commonly implemented in a printer or other motor controlled equipment. In contrast with other scanning approaches, this mask 432, which serves only to pass a selected beam or beams, is functionally not a critical moving optical component. Alternatively, a liquid crystal or other non-moving mask may be used which can greatly decrease the remaining motion dead-time associated with mask stepping movements.

The short term index of refraction sensitivity δn of the optical interrogation system 100b can be determined by testing with specimens that invoke known index of refraction changes Δn at the sensor 402 (see FIGS. 6A-6C). The potential sensitivity of the measurement system 100b and sensor 402 can be defined as one standard deviation of the noise in the pixel baseline (after linear drift subtraction) divided by the pixel shift Δx observed after the application of that known index specimen as indicated by the following equation:

$$\delta n = \frac{Std. Dev}{\Delta x} * \Delta n \qquad (2)$$

As shown in FIGS. 5A, 6A and 7, the resonant responses from the sensors 402 occupy almost the entire vertical dimension of the image from the CCD detector 430. Since the data are integrated along the vertical direction when angular response shifts are measured, the signal intensity in the direction transverse to the sensor angular response is redundant information. As such, the readout and data processing may be made faster by acquiring and analyzing data from a reduced region of the screen using common windowing (also known as "region of interest") algorithms. Alternatively, the integration of the responses from sensors 402 lying in the vertical direction may be accomplished in whole or in part by inserting a cylindrical optic (not shown in FIG. 4) in the receive path either prior to or after the spherical optic 428. This creates an anamorphic receive optical system which is described in greater detail below with respect to the optical interrogation system 10c shown in FIGS. 8A and 8B.

Figure 8A:
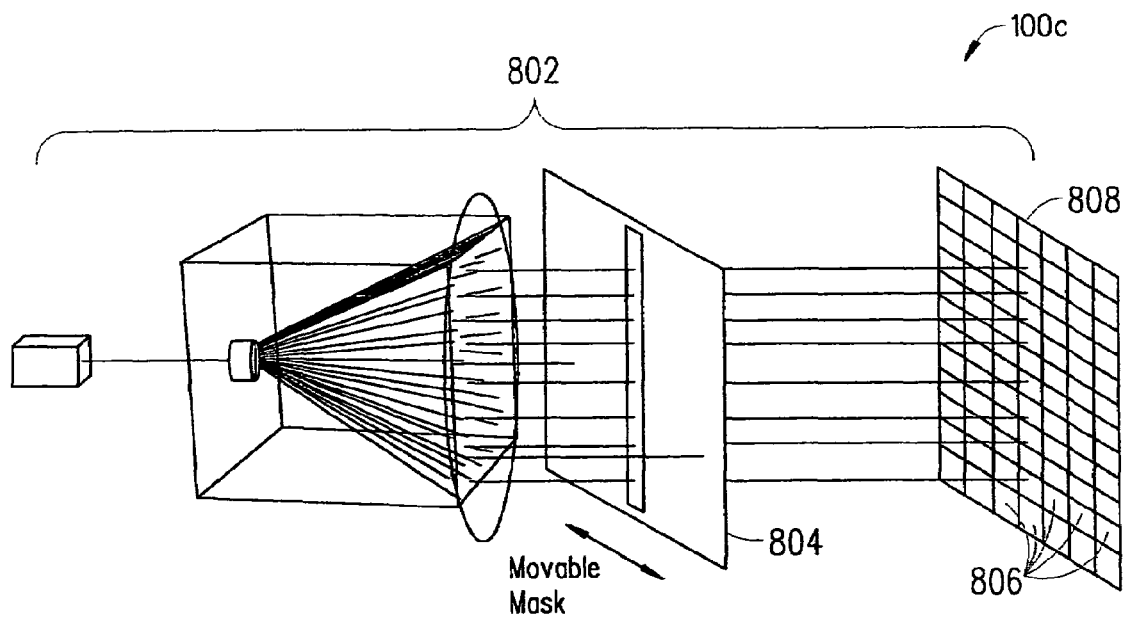

Referring to FIGS. 8A and 8B, there are block diagrams of a launch system 802 and an anamorphic receive system 810 that are used in an optical interrogation system 100c that is configured in accordance with a third embodiment of the present invention. FIG. 8A shows in greater detail the components in the launch system 802 that includes a mask 804 with a vertical slit which lets beamlets pass to a column of sensors 806 at the sensor array 808. For a more detailed discussion about this particular launch system 802 and other launch systems that can be used reference is made to U.S. patent application Ser. No. 10/602,304. FIG. 8B shows a schematic of the anamorphic re-focusing technique. In particular, the cylindrical optic 812 can be introduced into the receive path to anamorphicly re-focus the response light 816 from a column (vertical) of sensors 808 lying in the direction transverse to the sensor response directions (horizontal). The dashed arrows signify the focal point of the spherical lens 814 without the introduction of the cylindrical optic 812. The transverse direction focal point can lie behind or in front of the plane of the detector 818. The anamorphic re-focusing technique performs a partial integration function (optically) on the sensor response data by directing the light 816 in the transverse direction onto a smaller group of pixels in the detector 818. The anamorphic focusing technique can also be made to separate the sensor responses from adjacent rows such that they can occupy different regions in the vertical direction on the detector 818. It should be appreciated that by using this method the responses from many rows of sensors 806 can be accommodated onto a single detector image for simultaneous measurement with each frame acquisition. The mask 804 then blocks all beamlets except those directed at the sensors in the column of interest and thus allows simultaneous measurement of a column of sensors 806 in the array 808. This mask may be moved rapidly and with low precision to allow rapid serial measurement of all columns in the array.

To accomplish all of this the cylindrical optic 812 should be oriented such that it will condense the response signal along the direction transverse to the sensor angular response direction. The plane of the detector 818 may need to be re-positioned slightly relative to the spherical lens 814 to accommodate for the focal shift incurred by the signal beams 816 when passing through the cylindrical optic 812. It should also be appreciated that the spherical optic 814 and cylindrical optic 812 can be used in a wide variety of optical interrogation systems like the ones described herein and in U.S. patent application Ser. No. 10/602,304.

The use of the anamorphic focusing technique where the cylindrical optic 812 can be chosen to anamorphically re-focus and resolve the signals 816 from multiple sensors 806 simultaneously on the same detector 818 has at least two advantages:

It condenses the redundant information along the axis transverse to the angular response axis into a smaller area on the detector 818.

The response from each row of sensors 806 can be re-directed to occupy different regions on the plane of the detector 818.

Software can then divide the image up into regions of interest that are associated with each row of sensors 808 and any remaining vertical integration of the sensor responses in each region may be completed by using computer software as described below with respect to FIGS. 9-10.

FIGS. 9A and 9B are two simulation images used to help clarify the operation of the anamorphic receive system 810 shown in FIG. 8B and to explain a method for camera data analysis. If the column mask 804 was removed, one would obtain the responses from many sensors 806 in the image from the detector 818 as shown in FIG. 9A. With the mask 804 in place (blocking the beamlets in all but one column of sensors 806) one would obtain the responses from the sensors 806 in a single column as shown in FIG. 9B. Software may then be used to select regions of interest (see individual boxes) and thus simultaneously measure the responses from an entire column of sensors 806. In particular, the software may integrate the vertical pixel data in each of the regions of interest corresponding to each row of sensors 806 which enables simultaneous measurement of a column of sensors 806 with each frame acquisition. And, the vertical mask 804 can be moved or switched along the horizontal direction to allow rapid interrogation of a large two-dimensional array of sensors 808.

Figure 10A:
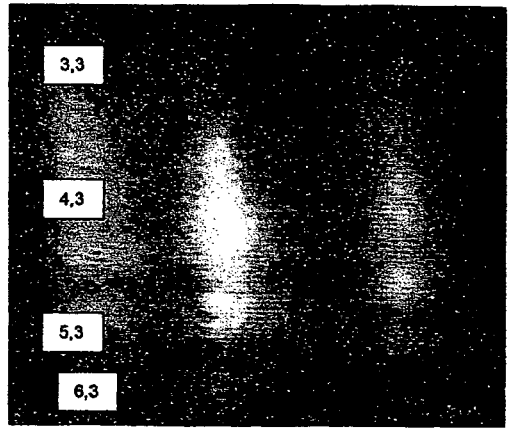
FIGS. 10A-10C are two images and a graph that were obtained from another experiment which are used to further help describe the operation of the anamorphic receive system shown in FIG. 8B.
Figure 10B:
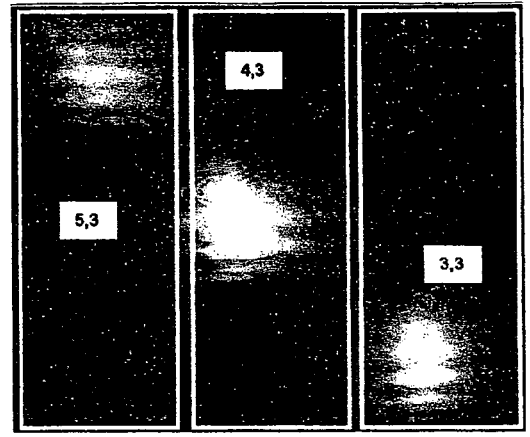
Figure 10C:
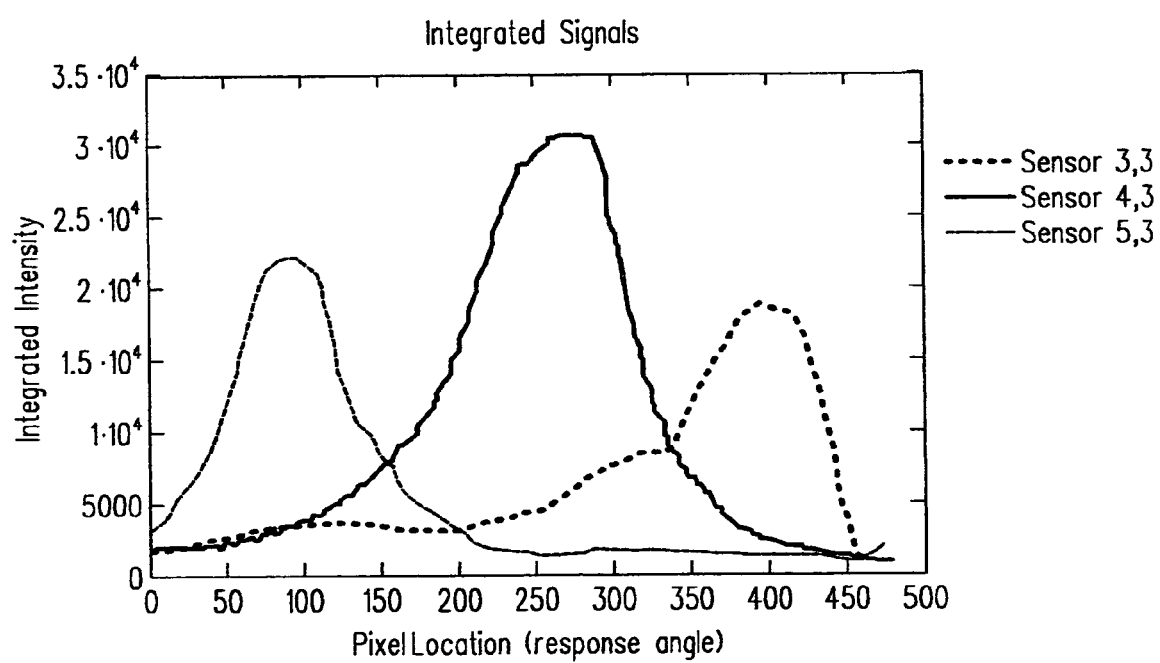

FIGS. 10A-10C are two images and a graph that were obtained from yet another experiment which are used to further help clarify the operation of the anamorphic receive system 810 shown in FIG. 8B and to explain a method for camera data analysis. In this experiment, responses from 30 sensors 806 spanning a circular region of 45 mm diameter were successfully imaged onto the 4.8 mm×6.4 mm CCD camera 818 by the use of a 3 inch diameter receive lens 814. A column mask 804 was used to allow passage of the responses from a single column of sensors 806 through the receive system 810. FIG. 10A shows the resulting image before insertion of a 100 mm focal length cylindrical lens 812 as shown in FIG. 8B. Responses from four of the sensors (3,3)-(6,3) were observed. Insertion of the cylindrical lens 812 created an anamorphic condition, separating the sensor responses onto different regions of the CCD detector 818 as well as partially integrating the signals from each sensor 806 as can be seen in FIG. 10B. The $4^{th}$ sensor response (6,3) shown in FIG. 10A lies outside the area of the CCD detector 818. FIG. 10C is a graph that shows the three integrated resonance angle responses from sections of the CCD image associated with each sensor 806. This data was obtained using the embodiment of the optical interrogation system 100a as described in FIG. 2 and with the anamorphic receive system 810 described in FIG. 8B.

As can be seen, the mask 804 allows illumination of a single column of sensors and at the same time blocks all of the responses amongst sensors 806 on the same row except the sensors 806 in the column of interest, thus eliminating cross-talk (see FIGS. 8A, 8B, 9A and 10A-10C). The mask 804 may then be scanned or switched to allow parallel detection from multiple sensors 806 and to allow the serial sampling of every row of sensors 806 in the array 808. An advantage of the anamorphic receive method is that the measurement speed may be increased by a factor equal to the number of rows of sensors 806 simultaneously and separately imaged onto the plane of the detector 818. This can also help to decrease the number of parallel optical receive systems needed to measure the array 808 in a small time period. The anamorphic optical receive system 810 may utilize spherical and cylindrical optics 812 and 814, anamorphic prisms, or specially designed anamorphic lenses.

The anamorphic technique described above should be contrasted with the technique described in U.S. Pat. No. 5,313,264. An anamorphic receive detection method is used in that patent to in order to detect SPR responses from rows of sensors simultaneously. However, that system maps the angular response from a 1-dimensional line of sensors onto a 2-dimensional plane. Mapping of a 2-dimensional array of sensors must be accomplished by scanning critical components (such as optics or the sensor array) in the system. In contrast, the presently described invention maps the angular response from a 2-dimensional array of sensors 808 onto a smaller 2-dimensional detector plane 818 by allowing more than one sensor 806 in a row to direct its response to span the same pixels on the detector as other sensors 806 in the row. The column masking technique then allows the same angular measurement region to be used serially (in time) across the row of sensors 806 and at high speed without the possibility of cross-talk between sensors in that row. This aspect of no critical moving optical components is particularly important when the angular measurement requires very high sensitivity and repeatability in the measured angular response.

Figure 11:
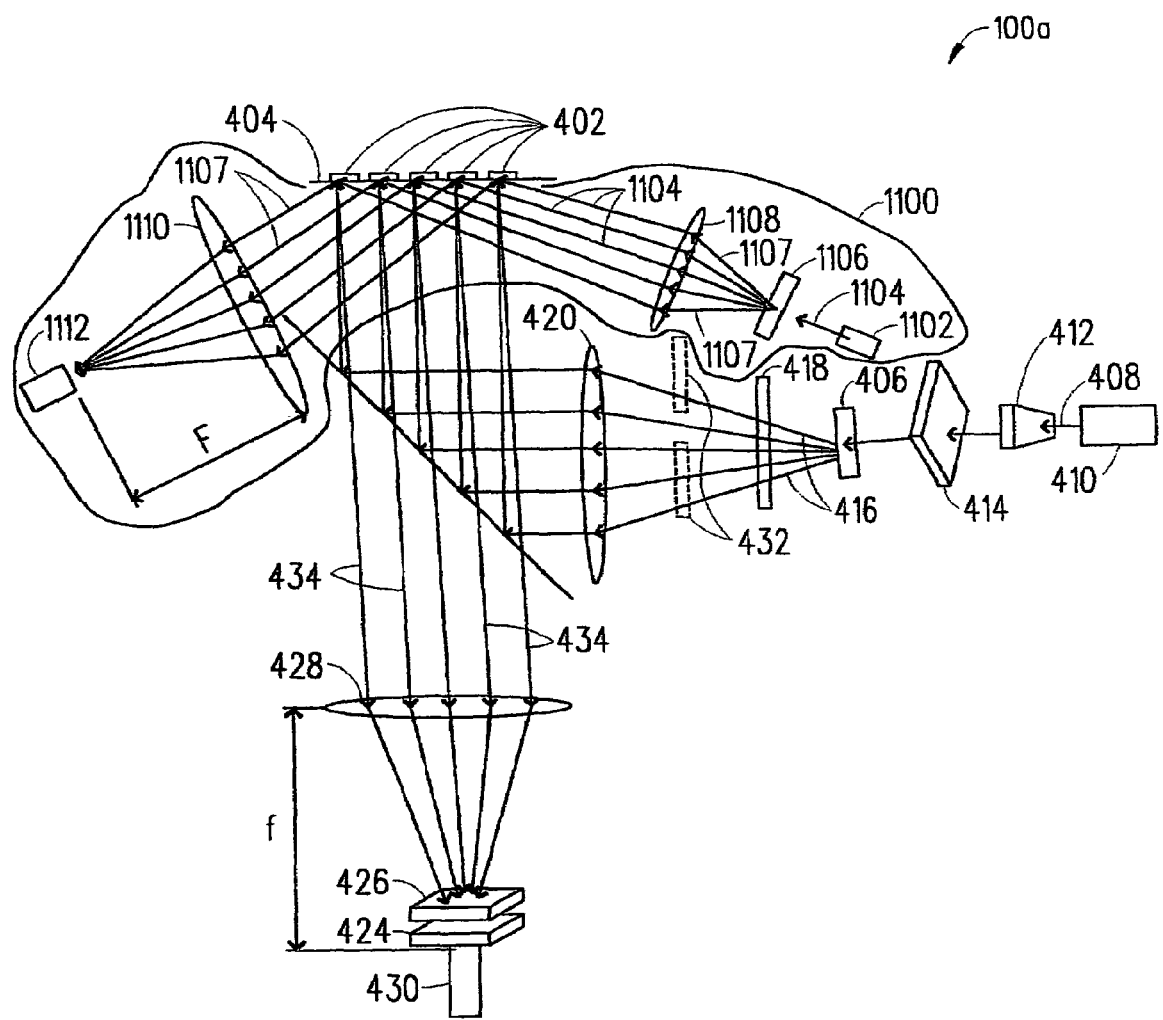
FIG. 11 is a block diagram of the optical interrogation system shown in FIG. 4 that has an angular measurement system added to it which is used to measure the angular change of the plane of a sensor array whenever the sensor array is repositioned or removed and returned in the system in accordance with a fourth embodiment of the present invention.

Referring to FIG. 11, there is a block diagram of the optical interrogation system 100a shown in FIG. 4 that has an angular measurement system 1100 which is used to measure the angular change of the plane of the sensor array 404 when that sensor array 404 is repositioned or removed and then returned to the system in accordance with another embodiment of the present invention. Basically, the angular measurement system 1100 can be used to enable the sensor array 404 to be removed and replaced without causing degradation of the angular measurement accuracy. As shown, the angular measurement system 1100 includes a light source 1102 that emits a light beam 1104 which is collimated and then directed at and reflected by the sensor array 404 to a reverse auto-collimating lens 1110 which focuses the reflected beam 1107 onto a CCD or other position measuring detector 1112. This detector is placed at the focal length of the lens. More generally, it is also possible to use a diffractive optic 1106, a mask (not shown) and a beamlet collimating lens 1108 to generate an array of collimated beamlets 1107, which are directed at the sensor array 404. Then the angular shift of sensor array can be measured at one or a number of points when the array is removed and then re-inserted into the instrument. Hence the angular shift caused by removal and re-insertion of the sensor array can be measured and then subtracted from each measured sensor's angular response. The wavelength of the light source 1102 (e.g., LED 1102) should be chosen such that the collimated beams 1107 do not interact with the measured sensor response 434. The angular measurement system 1100 may be oriented parallel to (as shown) or transversely to the sensor response measurement system. In the case of where the light source 1102 is an LED 1102, then the short coherence length can ensure that interference fringes will not be observed at the detector 1112. In operation, the small area CCD detector 1112 measures the beam 1104 deflections associated with the change in the angular location of each sensor 402 upon its being returned to the instrument 100a, as given below by equation no. 3. The net angular shift of the response from the sensor 402 after it is removed and replaced in the instrument 10a is the difference of the measured resonance angle response 434 and the reflected angle changes 1107 (see equation no. 4).

In this embodiment, the change in angle ΔØ of the surface normal at each location in the array 404 is equal to:

$$\Delta\phi = \Delta X/2F \tag{3}$$

Comparing to Equation 1, the factor of 2 originates from the fact that the geometrical angular reflection change of a beam is twice the angular change in the surface normal. With the appropriate choice of focal length F, the geometrical reflection change resolution can be made as sensitive as required to ensure that the re-insertion angle is measured as accurately as (or more accurately than) the resonance response change. The net angular shift ΔΨ of just the sensor resonance angle before and after the re-insertion of the sensor plate 404 may then be determined by the difference between total measured angular change (Δθ measured by beams 434) and the measured change in sensor plane tilt angle (ΔØ measured by beams 1107) as shown in equation no. 4:

$$\Delta\Psi = \Delta\theta - \Delta\phi \tag{4}$$

Referring still to the optical interrogation system 100b shown in FIG. 4 it should be noted that the read-out time of a 12×8 (96) sensor plate 404 can be estimated by considering that, in the experimental data from FIGS. 6B, 6C and 7 frames were summed for each time data point at a rate of 30 frames per second, which is approximately ⅓ of a second per time point. The mask 432 can be switched between positions in less than ½ second. Thus using a mechanical mask 432 with an anamorphic receive system 810 (see FIG. 8B) it can be estimated that the 12 rows of sensors 404 can be read in approximately 10 seconds. If a liquid crystal or similar non-moving mask 432 is used, then the time required by the motion of the mask 432 can be nearly eliminated and the net time is reduced to 4 seconds. Furthermore, the sensor array 404 can be divided into sub-sections where each sub-section has its own dedicated optical components and hardware for measurement of more responses in parallel. The mask 432 may have any required pattern and movement path such as to enable serial measurement of sensors 402 within the group associated with each sub-section (see U.S. patent application Ser. No. 10/602,304). This parallel detection system has the benefit of further increasing array measurement speed. For example, the array 404 can be divided into 4 optical sub-sections without too much of an increase in cost and complexity (see U.S. patent application Ser. No. 10/602,304). Then it is possible to use the present invention with, for example, a liquid crystal mask 432 to measure every sensor 402 in a 96 sensor array 404 in as little as 1 second. This fast read-out rate also has the advantage of increasing sensor accuracy and sensitivity for detecting binding events that could otherwise be limited by longer-term baseline drift and environmental influences in the measured response angle. This also allows faster kinetic measurements to be made in arrayed assay form.

It should be appreciated that the different embodiments of the optical interrogation system 100 can be scaled to read 1, 8, 24, 48, 96, 384, 1536 or other formats of a standard array simply by replacing the diffractive optic 212 or 406 (see FIGS. 2 and 4). Alternatively, the focal length of the spherical mirror 216 or lens 420 (see FIGS. 2 and 4) can be changed and the mirror re-positioned accordingly. In addition, non-standard formats can be accommodated in the same ways. Yet another approach would be to generate a sufficient number of beamlets to cover a densely packed sensor array and then step a mask with the appropriate apertures in one or two dimensions. In this manner, the same optical interrogation system 100 may be used to measure sensor arrays of varying densities. For example, a mask with 9 mm separations between apertures would be moved by 2.25 mm increments for a 1536 sensor array, 4.5 mm increments for a 384 sensor array and 9 mm increments for a 96 sensor array. Various mask patterns and stepping algorithms may be used to allow a desired sequence of sensor measurements in the array.

Figure 12:
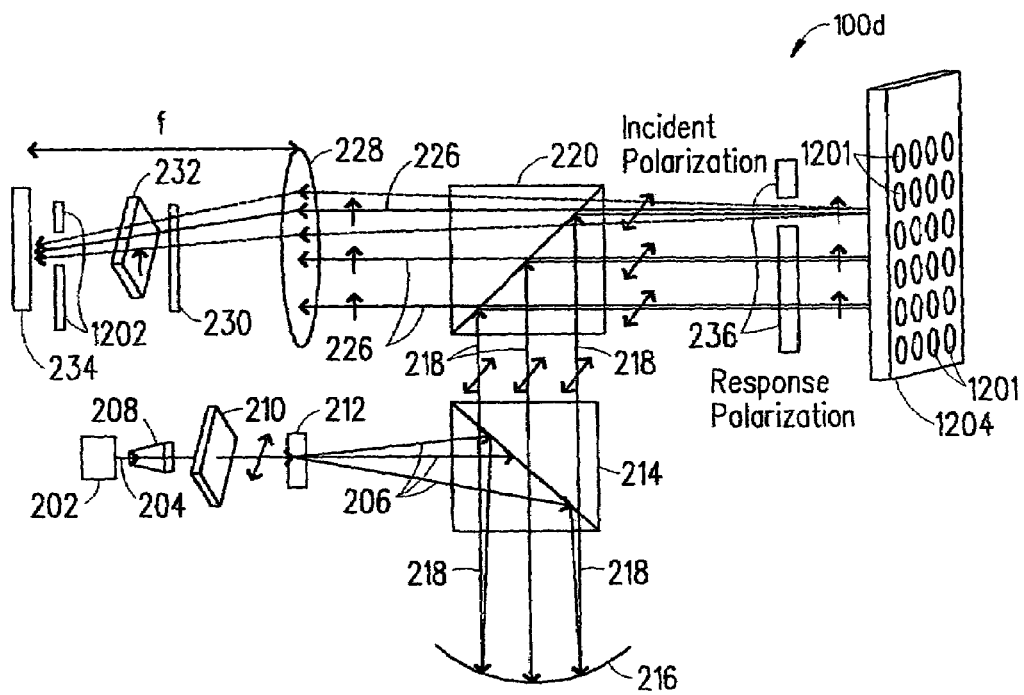
FIG. 12 is a block diagram of an optical interrogation system similar to the one shown in FIG. 2 except configured in accordance with a fifth embodiment of the present invention so it can be used for the purpose of intensity measurements such as might be required in a fluorescence based assay.

Referring to FIG. 12, there is a block diagram of an optical interrogation system 10d similar to the one shown in FIG. 2 except configured in accordance with yet another embodiment of the present invention so it can be used for the purpose of intensity measurements such as would be required in a fluorescence based assay. In the optical interrogation system 100d, the intensity of a signal emanating from a well 1201 is the quantity to be measured, and that quantity may or may not be an angular change and it may or may not be polarization specific. In such an intensity based assay, the 2-dimensional area on the detector 234 would be integrated over both dimensions of the region of interest to yield a single O-dimensional (i.e. a scalar) intensity data point. An additional numerical aperture (NA) restriction mask 234 may be placed in the optical receive system prior to the focusing optic 228 to restrict and equalize the numerical apertures of the signals from each well region before the signal 226 is passed to the detector 234. The signal transduction mechanism may be any type of scattering, reflection, transmission, or emission. In the case of fluorescence measurements, the beamsplitter 220 that lies prior to the sensor array 1204 may be dichroic, which would help to increase throughput efficiency and isolate the excitation wavelengths from the sample emission wavelengths.

It should also be appreciated that with respect to the optical interrogation system 100d, the polarizer 210 and analyzer 232 need not be used or they may be rotatable such as is required in a fluorescence polarization assay 1204. The beam 204 may be scanned by use of a mirror (not shown) or other means, or it may be divided as with a diffractive optic 212 (as shown). In the case of a diffractive optic 212, the mask 236 selects which well 1201 is to be illuminated and read. In the case of a scanning mirror, the sensor mask 236 is not required. It should further be appreciated that the reflection from the scanning mirror 216 is implied but not shown in FIG. 12.

Figures 13A, 13B:
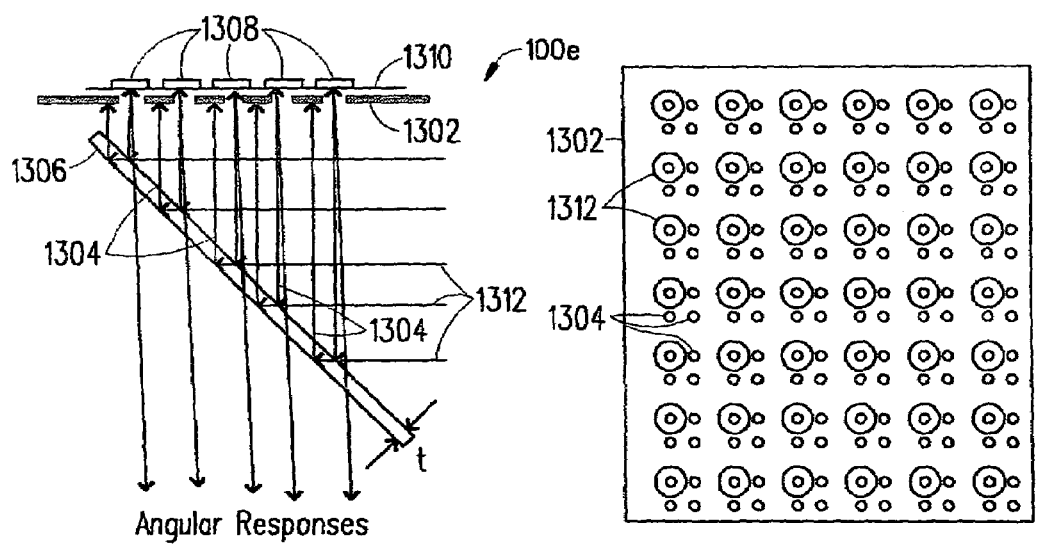
FIGS. 13A-13G are several diagrams used to describe how an optical interrogation system that has an aperture array can be used to block ghost reflections in accordance with a sixth embodiment of the present invention.

Referring to FIG. 13A, there is a block diagram of an optical interrogation system 100e that has an aperture array 1302 which is used to block "ghost" reflections 1304 originating from a plate type beamsplitter 1306 in accordance with yet another embodiment of the present invention. The ghost reflections 1304 create high frequency interference patterns across the detector which show up in the measured angular response, making it impossible to measure shifts in the sensor response angle with high (sub-pixel) accuracy. Hence when using large plate-type beamsplitters, there is a need for the aperture array 1302. In this embodiment, the beamsplitter 1304 is chosen to be thick enough (thickness "t") such that the apertures 1302 can block the ghost reflections 1304 and thin enough so that the ghost reflections 1304 from one beamlet 1312 do not impinge upon other sensors 1308 in the array 1310. The size of the aperture 1302 is chosen so as to transmit the entirety of the primary beamlet 1312 reflected from the first surface of the plate beamsplitter while blocking light originating from multiple reflections within the beamsplitter. This modification diminishes the dependence upon high quality and narrow band anti-reflection coatings on the beamsplitter faces, which are normally used to diminish the amplitude of the ghost reflections 1304. This concept can be incorporated into any of the previously described optical interrogation systems 100a, 100b, 100c and 100d.

FIG. 13B is a diagram of the spot pattern observed at the aperture array 1302 when using plate beamsplitters instead of the cube-type beamsplitters 214 and 220 shown in FIG. 2 in system 10b. These plate beamsplitters 214 and 220 were anti-reflection coated to operate at a wavelength that was not appropriate for the laser. The spot pattern consisted of the array of primary beamlets 1312 reflected from the first surfaces of both of the plate beam splitters as well as 3 additional arrays of ghost refection beamlets 1304 from the same plate-type beamsplitters located at positions 214 and 220. Only the array of primary beamlets 1312 was allowed to be transmitted through the aperture array 1302 to impinge upon and to be reflected from the sensor array 1310. In this case, the optical launch system and first beam splitter 214 were oriented at 90° to that shown in FIG. 2, which is a direction on the figure that would physically go into the page This produced the square arrangement of primary spots 1322 and ghost spots 1304 observed in FIG. 13B.

Figure 13C:
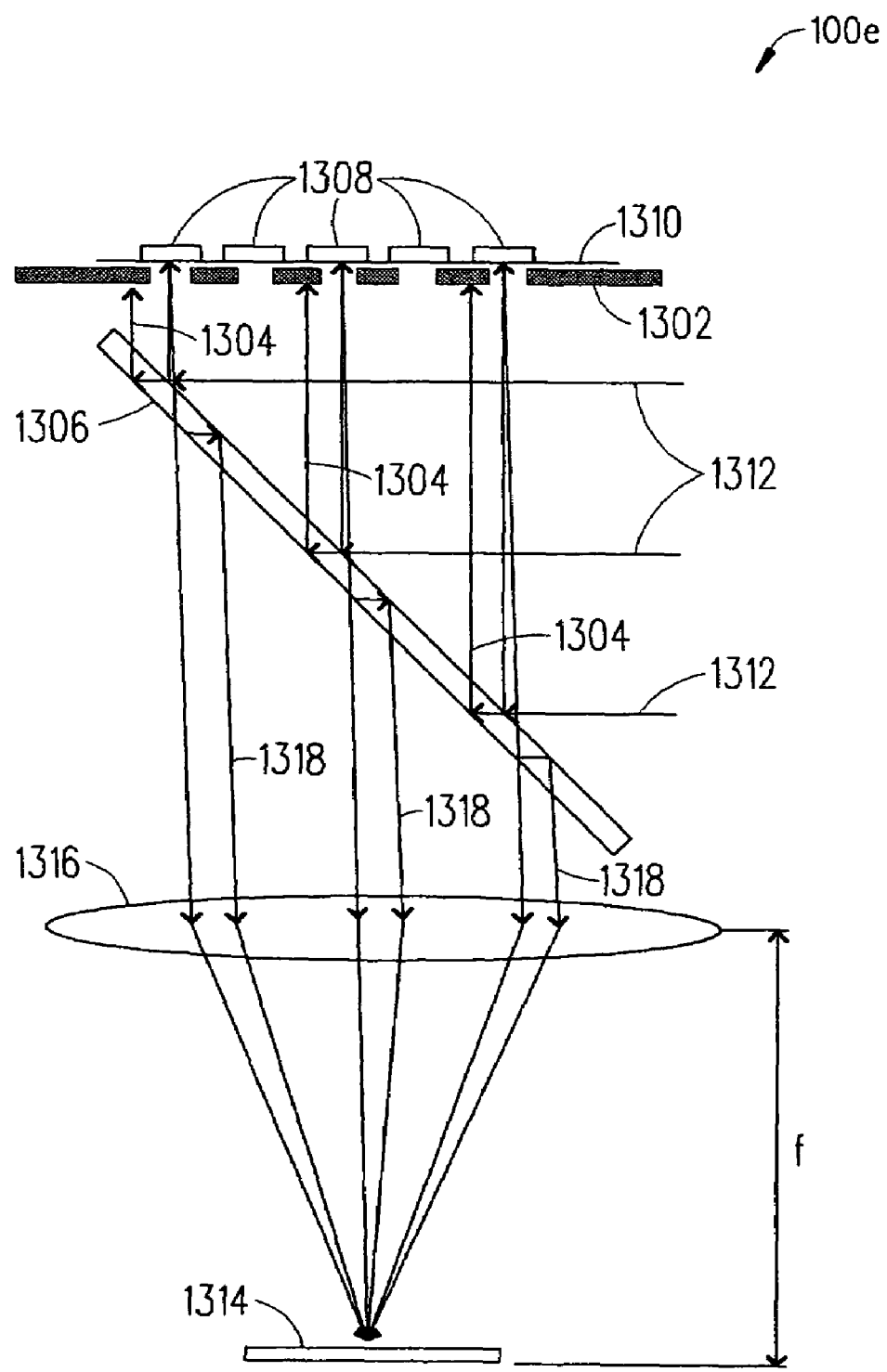

FIG. 13C illustrates another advantage of placing the detector 1314 at the focus of a reverse auto-collimating optic 1316: the interference effects at the detector 1314 caused by beamsplitter ghost reflections 1318 are eliminated. This occurs because the function of the receive system configuration is to map the sensor signals 1312 propagating at the same angle to the same location on the detector 1314 and this includes ghost reflections 1318 of the signal 1312 at the plate beamsplitter 1306. This effect of course depends upon the parallelism of the plate beamsplitter (wedged beamsplitting optics would not work). It should be noted that for clarity the signals 1312 from every other sensor 1308 were shown. Of course, a masking system like the ones described above can be used to select which sensor(s) 1308 is/are to be measured at any one time. It should also be noted that an image reduction receive method (detector not located at the focus of the receive lens) would not be able to eliminate interference effects from signal ghosts 1318 created at the beamsplitter 1306 because the primary signal 1312 and the ghost signal 1318 would not spatially overlap at the detector 1314. Complete elimination of the ghost response signal effect can only occur when the detector is placed at the focus of the receive lens. This plate beamsplitter 1306 and aperture array 1302 arrangement was used with the optical interrogation system 100a from FIG. 2 to obtain the data in FIGS. 13D-13F.

Figure 13D:
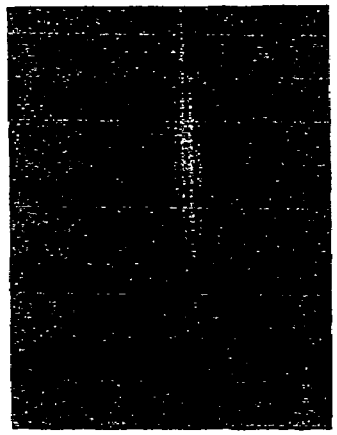
Figure 13E:
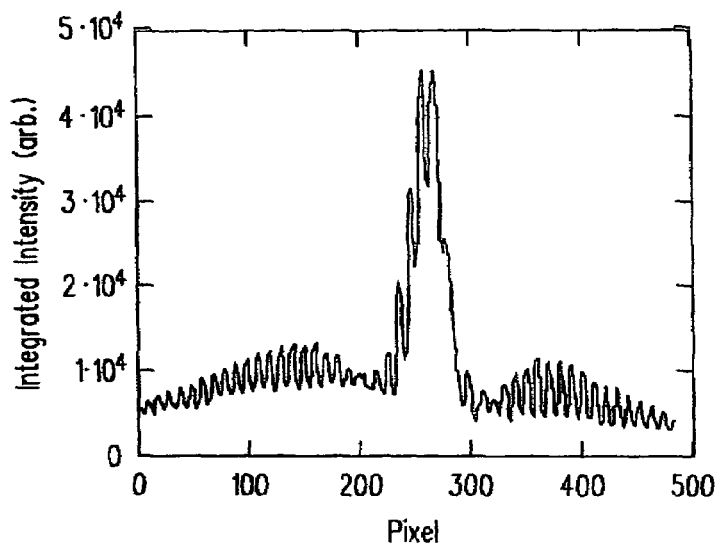
Figure 13F:
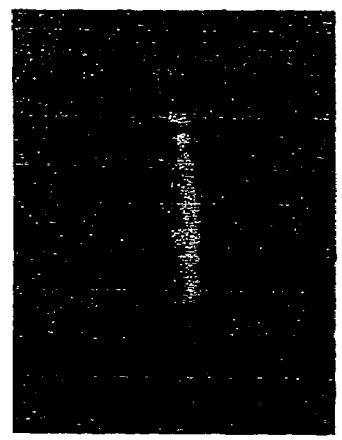
Figure 13G:
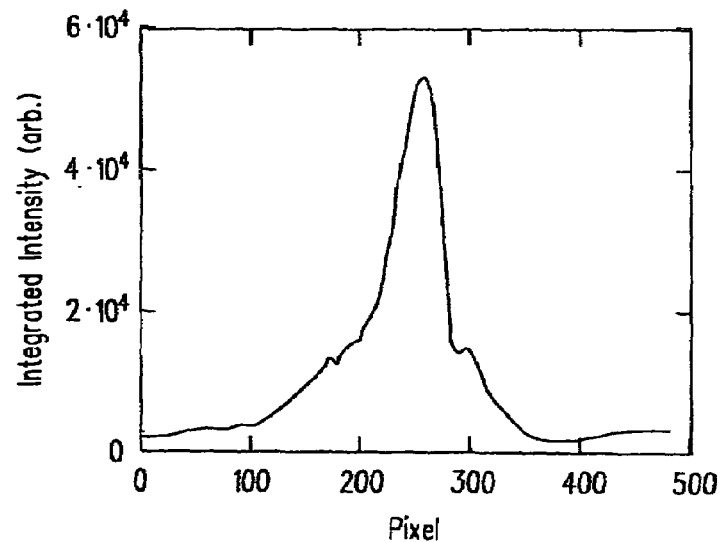

Referring to FIGS. 13D-13F, the aperture array 1302, the beamsplitter plate 1306, and far-field receive system 1314 and 1316 of FIG. 13C were used in combination with the beamlet mask 236 and the optical interrogation system 10a in FIG. 2 to obtain this angular resonance data. The beamsplitter plate 1306 had ghost reflections 1304 of sufficient amplitude that they could be easily observed visually on the aperture array 1302 located at the sensor plane 1310 (see FIG. 13B). FIG. 13D is a CCD image of the sensor response without the use of the aperture array 1302. Considerable high frequency interference can be observed in the image. FIG. 13E is a graph of the vertical integration of the image in FIG. 13D which clearly shows the effect of the ghost reflection interferences 1304. The ghost interferences 1304 make it impossible to measure angular shifts of the resonance with sub-pixel accuracy. FIG. 13F is a CCD image of the same sensor response as the image in FIG. 13D except with the inclusion of the aperture array 1302. FIG. 13G is a graph of the vertical integration of the image from FIG. 13F which shows that the interference effects of the ghost reflections 1304 from the beamsplitters 214 and 220 have been eliminated.

In yet another embodiment of the present invention it should be noted that position sensitive detectors (PSDs) may be used to perform the signal integration electronically without the use of software. Typically these PSDs report a single numeric value that indicates the centroid of the angular response from the sensor 1308. However, from a practical point of view, an array or linear CCD detector 1314 enables the entire response function to be analyzed by a variety of software algorithms and is therefore more able to cope with anomalies and noise in the imaged data. For example, a CCD based detection system and software can be used to select and analyze only the peak region of the signal and ignore extraneous information outside of the peak region. In contrast, small anomalies or noise situated outside of the peak region can significantly shift the centroid reported by a PSD. Therefore a CCD or other array-type detector 1314 is the preferred component for use in an optical detection system.

From the foregoing, it can be readily appreciated by those skilled in the art that the present invention solves an important problem in the high speed and accurate detection of angular responses associated with many sensors or specimens arranged in large area 2-dimensional arrays. This was accomplished by the present invention without optical angle scanning, mechanical scanning of critical components, use of numerous multiplexed components, use of extremely large area detectors, or use of large area illumination sources. Because the optical interrogation systems described herein have no critical moving parts, they allow measurement with high speed, accuracy, and sub-pixel repeatability. A further advantage of the present invention is that, by using small area detectors, faster detector read-out rates and lower cost may be obtained. Another advantage of the present invention is that the power from a light source may be conditioned and directed to an array of samples with much higher efficiency in optical power and similarity across sensors in the array, in contrast to traditional flood illumination methods. Another advantage of the present invention is that by using simple and low precision masking, cross-talk amongst sensors can be eliminated. A further advantage of the present invention is that an anamorphic receive system may be added to allow multiple sensors to be read simultaneously with the same detector. Yet another advantage of the present invention is that the measurement time can be decreased by constructing the system to use multiplexed optical paths and hardware to whatever degree the cost, complexity, space, and reliability issues will allow. In yet another advantage of the present invention is that it may also be scaled easily from 96 sensor arrays (as described) to 384 and 1536 sensor arrays in the standard micro-array plate format of approximately 100 mm×70 mm.

It should be noted that many embodiments of the invention are described herein. Included in these descriptions are the technical reasons for using those embodiments. In the design of an optical measurement system it should be appreciated that various combinations of the described components may be included or omitted, as required, in order to create a measurement system with the desired degree of accuracy. It should also be understood that this invention includes all systems that would use combinations of the components described herein and the components described in U.S. patent application Ser. No. 10/602,304 where the need for those combinations would be apparent to persons familiar with optical technology.

It should be further noted that the simple optics depicted in the FIGURES herein are solely for illustrating the concept. Compound lenses or mirrors may be used in their place if required by the measurement technique. These optics may be simple lenses, aspheric lenses, F-θ lenses, telecentric lenses, beam expanders, curved mirrors of various types, prisms or combinations thereof which are needed to achieve the required optical properties of beamlet or signal collimation, focusing, parallel propagation, equal spacing, polarization, aberration control, or anamorphic focal conditioning. Component functions (such as polarizers and beamsplitters) may be used as individual components in the system or combined with other component functions (such as polarizing beamsplitters) to accomplish the same system objectives as described herein. This also includes anamorphic optical functions which may be created by a combination of cylindrical and spherical optics, anamorphic prisms, or specially designed anamorphic lenses.

In the angular interrogation methods of the present invention, optical power existing in the range of angles corresponding to the sensor response can be either removed from the beam (producing a dark line in the far-field image) or can be resonantly enhanced (producing a bright line in the far-field image) through transmission, absorption, or reflection. If the resonance is sufficiently broad to span many pixels of the receiver, then it is possible to use peak smoothing and fitting algorithms on the resonance data to detect shifts of the resonant response with sub-pixel accuracy. Typically sub-pixel sensitivity on the order of hundredths of a pixel is readily achievable. Given that pixels of CCD cameras are on the order of 10 μm wide, this means that resonance shifts of approximately 100 nm are detectable at a CCD detector plane. In order to fully utilize this potential sensitivity, an optical interrogation system should be very precise and very repeatable with respect to monitoring of the response of the sensors in the array. This is provided by the present invention.

Following are some advantages and uses of the optical interrogation systems and methods of the present invention:

The optical interrogation systems provide a simple and efficient means of generating an array of beams with precisely controlled spacing and optical characteristics at the specimen array.

The optical interrogation systems have a minimum number of or no moving parts.

The optical interrogation systems do not require precise movement or alignment of its components to optically interrogate rows and/or individual sensors in the specimen array.

The optical interrogation systems allow a large number of specimens to be interrogated simultaneously.

The optical interrogation systems could be applied in the following applications (for example):

Grating and non-grating based sensors.

Fluorescence, scattering, emission, reflection, transmission angle, infrared and ultra-violet absorption spectroscopy, Fourier transform infrared absorption (FTIR) spectroscopy, Raman spectroscopy, reflection spectroscopy, fluorescence spectroscopy, fluorescence lifetime spectroscopy, and surface plasmon resonance spectroscopy.

The present invention also has the following advantages:
(1) Rapid, accurate, efficient, and highly repeatable optical illumination of an array of sensors.
(2) The measurement of the angular responses from each sensor in the array with high accuracy even when those sensors are distributed over a relatively large 2-dimensional area.
(3) Keeping the complexity and costs of building and servicing the instrumentation low. This implies using the fewest possible low cost optical components such as lasers, optics, detectors, and hardware.
(4) Ensuring that the instrumentation provides a uniform illumination and response capability for all locations in the array.
(5) Removing and replacing the sensor array without seriously degrading the accuracy of the measurement of the angular responses of the sensors.

The specific application to which the present invention has been applied is that of measuring the angular shift in the resonantly reflected light from a surface grating waveguide index of refraction sensor. The change in resonance angle indicates changes in the index of refraction at the surface of the sensor. The surface index of refraction changes can be due to:
(1) The displacement of one material or liquid by another material or liquid at the surface (for example in a surface binding assay).
(2) The response in relation to changes in temperature, pressure, humidity, a reaction, material absorption, etc. at the surface of the sensor.

It should be noted that the results demonstrated in the present invention were obtained with sensors which are grating-coupled waveguide sensors. The following document discloses details about the structure and the functionality of exemplary sensors that can be used in the present invention:
(1) U.S. Pat. No. 4,815,843 entitled "Optical Sensor for Selective Detection of Substances and/or for the Detection of Refractive Index Changes in Gaseous, Liquid, Solid and Porous Samples".

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. An optical interrogation system comprising:
a launch system for generating an array of light beams and for simultaneously controlling the numerical aperture, focus, and polarization of said light beams while also directing all or a predetermined number of said light beams towards a large area two-dimensional specimen array; and
a receive system for receiving all or a predetermined number of responses from said light beams reflected from sensors or specimens in said large area two-dimensional specimen array, wherein said receive system has a far-field diffraction measurement configuration where a reverse auto-collimating optic simultaneously receives all or the predetermined number of said light beams reflected from sensors in the large area two-dimensional specimen array and focuses those light beams at a small area detector in the receive system.

2. The optical interrogation system of claim 1, wherein said receive system is configured to enable fluorescence assay measurements, infrared and ultra-violet absorption spectroscopy, Fourier transform infrared absorption spectroscopy, Raman spectroscopy, reflection spectroscopy or surface plasmon resonance spectroscopy.

3. The optical interrogation system of claim 1, wherein:
said launch system includes a mask that blocks a certain number of said light beams from reaching selected sensors or specimens in the large area two-dimensional specimen array; or
said receive system includes a mask that blocks a certain number of said light beams reflected from selected sensors or specimens in the large area two-dimensional specimen array.

4. The optical interrogation system of claim 1, wherein grating based sensors are located in the large area two-dimensional specimen array.

5. The optical interrogation system of claim 1, wherein said large area two-dimensional specimen array is a multi-well plate.

6. An optical interrogation system comprising:
a launch system for generating an array of light beams and for simultaneously controlling the numerical aperture, focus, and polarization of said light beams while also directing all or a predetermined number of said light beams towards a large area two-dimensional specimen array; and
a receive system for receiving all or a predetermined number of responses from said light beams reflected from sensors or specimens in the large area two-dimensional specimen array, wherein said receive system has an anamorphic re-focusing configuration where a cylindrical optic is inserted in a receive path either prior to or after a spherical optic to enable parallel detection and partial optical integration of all or the predetermined number of said light beams reflected from selected sensors in the large area two-dimensional specimen array.

7. An optical interrogation system comprising:
a launch system for generating an array of light beams and for simultaneously controlling the numerical aperture, focus, and polarization of said light beams while also directing all or a predetermined number of said light beams towards a large area two-dimensional specimen array;
a receive system for receiving all or a predetermined number of responses from said light beams reflected from sensors or specimens in the large area two-dimensional specimen array; and
an angular measurement system for measuring a change in angular tilt of a plane of the large area two-dimensional specimen array whenever the large area two-dimensional specimen array is repositioned or removed and returned.

8. An optical interrogation system comprising:
a launch system for generating an array of light beams and for simultaneously controlling the numerical aperture, focus, and polarization of said light beams while also directing all or a predetermined number of said light beams towards a large area two-dimensional specimen array;
a receive system for receiving all or a predetermined number of responses from said light beams reflected from sensors or specimens in the large area two-dimensional specimen array; and
an aperture array used to prevent ghost reflections of light beams from a beamsplitter and other optical elements from reaching the large area two-dimensional specimen array.

9. A method for interrogating one or more specimens in a large area two-dimensional specimen, said method comprising the steps of:
using a launch system to generate an array of light beams and direct all or a predetermined number of said light beams towards said large area two-dimensional specimen array; and
using a receive system to receive all or a predetermined number of said light beams reflected from said large area two-dimensional specimen array, wherein said receive system has a far-field diffraction measurement configuration where a reverse auto-collimating optic simultaneously receives all or the predetermined number of said light beams reflected from sensors in the large area two-dimensional specimen array and focuses those light beams at a small area detector.

10. The method of claim 9, wherein said receive system is configured to enable fluorescence assay measurements, infrared and ultra-violet absorption spectroscopy, Fourier transform infrared absorption spectroscopy, Raman spectroscopy, reflection spectroscopy or surface plasmon resonance spectroscopy.

11. The method of claim 9, wherein:
said launch system includes a mask that blocks a certain number of said light beams from reaching selected specimens in the large area two-dimensional specimen array; or
said receive system includes a mask that blocks a certain number of said light beams reflected from selected specimens in the large area two-dimensional specimen array.

12. The method of claim 9, wherein grating based sensors are located in the large area two-dimensional specimen array.

13. The method of claim 9, wherein said large area two-dimensional specimen array is a multiwell plate.

14. A method for interrogating one or more specimens in a large area two-dimensional specimen, said method comprising the steps of:
using a launch system to generate an array of light beams and direct all or a predetermined number of said light beams towards said large area two-dimensional specimen array; and
using a receive system to receive all or a predetermined number of said light beams reflected from said large area two-dimensional specimen array, wherein said receive system has an anamorphic re-focusing configuration where a cylindrical optic is inserted in a receive path either prior to or after a spherical optic to enable parallel detection of all or the predetermined number of said light beams reflected from selected sensors in the large area two-dimensional specimen array.

15. A method for interrogating one or more specimens in a large area two-dimensional specimen, said method comprising the steps of:
using a launch system to generate an array of light beams and direct all or a predetermined number of said light beams towards said large area two-dimensional specimen array;
using a receive system to receive all or a predetermined number of said light beams reflected from said large area two-dimensional specimen array; and
using an angular measurement system to measure a change in angular tilt of a plane of said large area two-dimensional specimen array whenever said large area two-dimensional specimen array is repositioned or removed and returned.

16. A method for interrogating one or more specimens in a large area two-dimensional specimen, said method comprising the steps of:
using a launch system to generate an array of light beams and direct all or a predetermined number of said light beams towards said large area two-dimensional specimen array;
using a receive system to receive all or a predetermined number of said light beams reflected from said large area two-dimensional specimen array; and
using an aperture array to prevent ghost reflections of light beams from a beamsplitter and other optical elements from reaching said large area two-dimensional specimen array.

* * * * *